United States Patent [19]

Bergman et al.

[11] Patent Number: 5,378,838
[45] Date of Patent: Jan. 3, 1995

[54] BENZODIAZEPINE CHOLECYSTOKININ ANTAGONISTS

[75] Inventors: Jeffrey M. Bergman, Telford; Roger M. Freidinger, Lansdale; Mark G. Bock, Hatfield, all of Pa.

[73] Assignee: Merck & Co., Inc., Rahway, N.J.

[21] Appl. No.: 3,927

[22] Filed: Jan. 13, 1993

[51] Int. Cl.⁶ .................. C07D 243/24; A61K 31/55
[52] U.S. Cl. ................................................ 540/509
[58] Field of Search .................... 540/509; 514/221

[56] References Cited

U.S. PATENT DOCUMENTS

| 4,820,834 | 4/1991 | Evans et al. | 540/504 |
| 5,218,115 | 6/1993 | Bock et al. | 540/509 |

FOREIGN PATENT DOCUMENTS

| 0284256 | 9/1988 | European Pat. Off. |
| 0304223 | 2/1989 | European Pat. Off. |
| 411668 | 2/1991 | European Pat. Off. |
| 0434364 | 6/1991 | European Pat. Off. |
| 0434369 | 6/1991 | European Pat. Off. |
| 0508796 | 10/1992 | European Pat. Off. |
| 0508797 | 10/1992 | European Pat. Off. |
| 0508798 | 10/1992 | European Pat. Off. |
| 0508799 | 10/1992 | European Pat. Off. |
| 92/01683 | 2/1992 | WIPO |

OTHER PUBLICATIONS

Bradwejn, et al., Enhanced Sensitivity to Cholecystokinin Tetrapeptide in Panic Disorder, Soc. Neurosci. Abstr. 14(1), p. 291, (1988).
de Montigny, Cholecystokinin Tetrapeptide Induced Panic Attacks in Healthy Volunteers, Soc. Neuosci. Abstr. 14(1), p. 291, (1988).
Bradwejn, et al., Benzodiazepines Antagonize Cholecystokinin–Induced Activation of Rat Hippocampal, Neurones, Nature 312, p. 22, (1984).
De Montigny, Cholecystokinin Tetrapeptide Induced Panic-like Attacks in Healthy Volunteers, Arch. Gen. Psychiatry, 46, pp. 511–517, (1989).
Dourish, et al., Enhancement of Morphine Analgesia and Prevention of Morphine Tolerance in the Rat by the Cholecystokinin Antagonist L–364, 718 Pharm. 147, pp. 469–472, (1988).
Bouthillier, et al., Long-term Benzodiazepine Treatment Reduces Neuronal Responsiveness to Cholecystokinin: an Electrophysiological Study in the Rat, Eur. Jour. Pharm. 151, No. 1, pp. 135–138, (1988).
O'Neill et al. Morphine Induced Analgesia in the Rat Paw Pressure Test is Blocked by CCK and Enhanced by the CCK Antagonist MK–329, Neuropharmacology 28, No. 3, pp. 243–247 (1989).
Chang, et al., Biochemical and Pharmacological Characterization of an Extremely Potent and Selective Nonpeptide Cholecystokinin Antagonist, Proc. Natl. Acad. Sci., 83, pp. 4923–4926 (1986).
Bock, et al., Benzodiazepine Gastrin and Brain Cholecystokinin Receptor Ligands: L–365, 260, Journal of Medicinal Chemistry, 32, No. 1, pp. 13–16 (1988).

*Primary Examiner*—Nicholas Rizzo
*Attorney, Agent, or Firm*—Francis P. Bigley; Mark R. Daniel; Joseph F. DiPrima

[57] ABSTRACT

Benzodiazepine analogs of the formula:

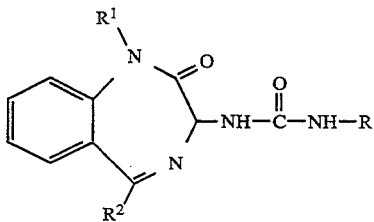

are disclosed which are antagonists of gastrin and cholecystokinin (CCK).

14 Claims, No Drawings

BENZODIAZEPINE CHOLECYSTOKININ ANTAGONISTS

FIELD OF THE INVENTION

This invention relates to the discovery of Benzodiazepine analogs of Formula I for use as antagonists of cholecystokinin (CCK) and gastrin when administered to animals, preferably humans.

BACKGROUND OF THE INVENTION

The Benzodiazepine analogs of Formula I of this invention are useful in treating various diseases caused by an excess of CCK or gastrin. Cholecystokinins (CCK) and gastrin are structurally related neuropeptides which exist in gastrointestinal tissue and in the central nervous system (see, V. Mutt, Gastrointestinal Hormones, G. B. J. Glass, Ed., Raven Press, N.Y., p. 169 and G. Nission, ibid, p. 127.

Cholecystokinins include CCK-33, a neuropeptide of thirty-three amino acids in its originally isolated form (see, Mutt and Jorpes, Biochem. J. 125,678 (1971)), its carboxyl terminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, TrP-Met-Asp-Phe-NH$_2$, which is the common structural element shared by both CCK and gastrin.

CCK's are believed to be physiological satiety hormones, thereby possibly playing an important role in appetite regulation (G. P. Smith, Eating and Its Disorders, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", Ann. Repts. Med. Chem. 17, 31, 33 [1982] and references cited therein; J. A. Williams, Biomed. Res. 3 107 [1982]; and J. E. Morley, Life Sci. 30, 479, [1982]).

The primary role of gastrin, on the other hand, appears to be stimulation of the secretion of water and electrolytes in the stomach, and, as such, it is involved in control of gastric acid and pepsin secretion. Other physiological effects of gastrin then include increased mucosal blood flow and antral motility. Rat studies have shown that gastrin has a positive trophic effect on the gastric mucosa, as evidenced by increased DNA, RNA and protein synthesis. See e.g. U.S. Ser. No. 452,023 filed Aug. 26, 1991, now abandoned.

Antagonists to CCK and to gastrin are useful for preventing and treating CCK-related and/or gastrin-related disorders of the gastrointestinal (GI) and central nervous (CNS) systems of animals, preferably mammals, and especially those of humans. Just as there is some overlap in the biological activities of CCK and gastrin, antagonists also tend to have affinity for both receptors. In a practical sense, however, there is enough selectivity for the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., Science 226, 1215 (1984)]. Selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value. See e.g. U.S. Pat. No. 4,820,834. It is further expected that the CCK antagonists of Formula I are useful anxiolytic agents particularly in the treatment of panic and anxiety disorders.

Since CCK and gastrin also have trophic effects on certain tumors [K. Okyama, Hokkaido J. Med Sci., 60, 206–216 (1985)], antagonists of CCK and gastrin are useful in treating these tumors [see, R. D. Beauchamp et al., Ann. Surg., 202,303 (1985)].

Distinct chemical classes of CCK-receptor antagonists have been reported [R. Freidinger, Med. Res. Rev. 9, 271 (1989)]. The first class comprises derivatives of cyclic nucleotides, of which dibutyryl cyclic GMP has been shown to be the most potent by detailed structure-function studies (see, N. Barlas et al., Am. J. Physiol., 242, G 161 (1982) and P. Robberecht et al., Mol., Pharmacol., 17,268 (1980)).

The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., Biochem. Biophys. Acta., 757, 250 (1983), and M. Spanarkel et al., J. Biol. Chem., 258, 6746 (1983)). The latter compound was recently reported to be a partial agonist [see, J. M. Howard et al, Gastroenterology 86(5) Part 2, 1118 (1984)].

The third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., Proc. Natl. Acad. Sci U.S.A., 78, 6304 (1981), R. T. Jensen et al., Biochem. Biophys. Acta., 761, 269 (1983)]. All of these compounds, however, are relatively weak antagonists of CCK (IC$_{50}$: generally 10$^{-4}$M[although more potent analogs of proglumide have been recently reported in F. Makovec et al., Arzneim-Forsch Drug Res., 35 (II), 1048 (1985) and in German Patent Application DE 3522506A1], but down to 10$^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., Science, 230, 177–179 (1985)] and 3-substituted benzodiazepines based on this structure [published European Patent Applications 167 919, 167 920 and 169 392, B. E. Evans et al, Proc. Natl. Acad, Sci. U.S.A., 83, p. 4918–4922 (1986) and R. S. L. Chang et al, ibid, p. 4923–4926] have also been reported.

No really effective receptor antagonists of the in vivo effects of gastrin have been reported (j. S. Morley, Gut Pept. Ulcer Proc., Hiroshima Symp. 2nd, 1983, p. 1), and very weak in vitro antagonists, such as proglumide and certain peptides have been described [(J. Martinez, J.

Med. Chem. 27, 1597 (1984)]. Recently, however, pseudopeptide analogs of tetragastrin have been reported to be more effective gastrin antagonists than previous agents [J. Martinez et al., J. Med. Chem., 28, 1874–1879 (1985)].

A new class of Benzodiazepine antagonist compounds has further been reported which binds selectively to brain CCK (CCK-B) and gastrin receptors [see M. Bock et al., J. Med. Chem., 32, 13–16 (1989)]. One compound of interest reported in this reference to be a potent and selective antagonist of CCK-B receptors is (R)-N-(2,3-dihydro-1-methyl-2-oxo-5-phenyl-1H-1,4-benzodiazepin-3-yl)-N$^1$-(3-methylphenyl) urea (See U.S. Pat. No. 4,820,834.) One disadvantage of the new CCK-B compound reported in Bock et al., J. Med. Chem., 32, 13–16 (1989) and U.S. Pat. No. 4,820,834, is that these CCK-B compounds are poorly water soluble.

It is, therefore, an object of the present invention to provide antagonists of CCK and gastrin. If an antagonist compound could be prepared which would bind with the cell surface receptor of CCK or gastrin, then the antagonist compounds of this invention could be used to block the effect of CCK and gastrin. Another object of the present invention is to provide novel CCK and gastrin antagonist compounds which are water soluble. Other objects of the present invention are to provide methods of inhibiting the action of CCK and gastrin through the administration of novel benzodiazepine analog compounds. The above and other object are accomplished by the present invention in the manner more fully described below.

SUMMARY OF THE INVENTION

The present invention provides Benzodiazepine analogs of the formula:

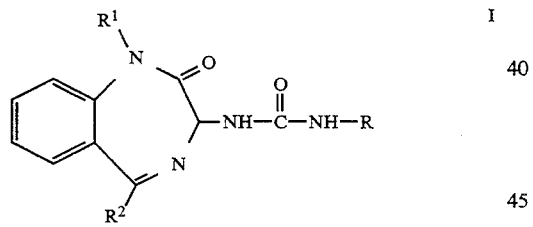

for use as antagonists of CCK and gastrin. The above-mentioned compounds can be used in a method of acting upon a CCK and/or gastrin receptor which comprises administering a therapeutically effective but non-toxic amount of such compound to an animal, preferably a human. A pharmaceutical composition comprising a pharmaceutically acceptable carrier and, dispersed therein, an effective but non-toxic amount of such compound is another aspect of this invention.

DETAILED DESCRIPTION OF THE INVENTION

Benzodiazepine analogs of Formula I provide antagonists of CCK and gastrin. The present invention further provides novel CCK and gastrin antagonist compound which are water soluble. The Benzodiazepine analogs of Formula I are useful in a method of antagonizing the binding of CCK to CCK receptors or antagonizing the binding of gastrin to gastrin receptors. The novel Benzodiazepine analogs of the present invention are illustrated by compounds having the formula:

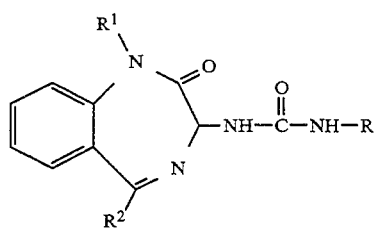

R is

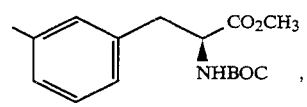

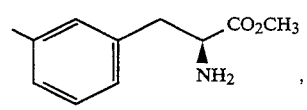

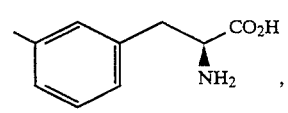

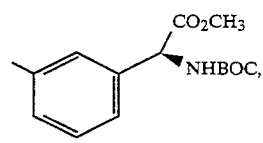

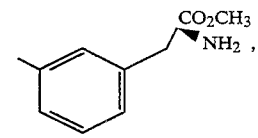

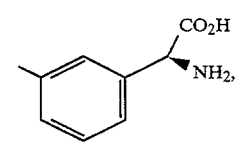

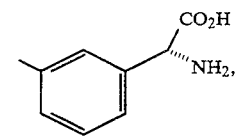

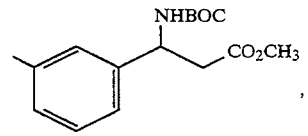

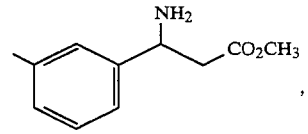

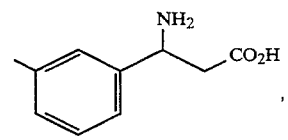

-continued

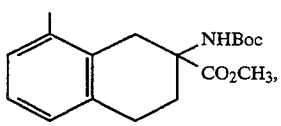

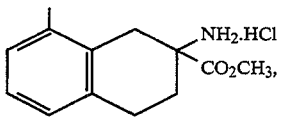

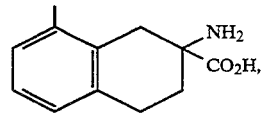

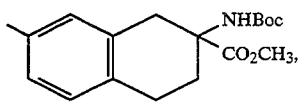

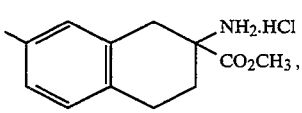

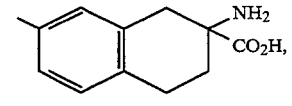

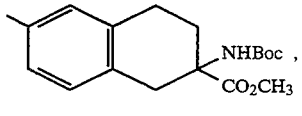

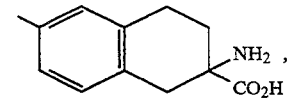

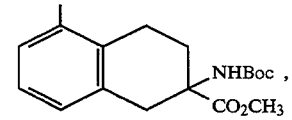

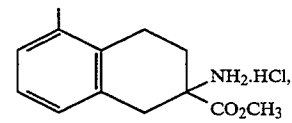

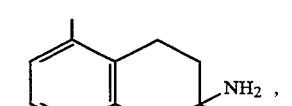

-continued

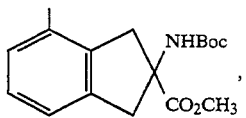

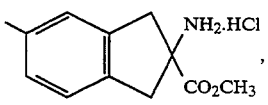

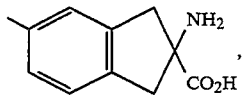

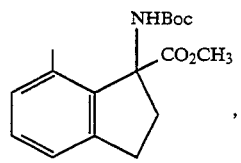

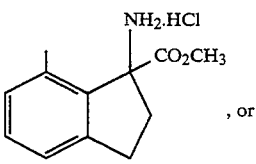

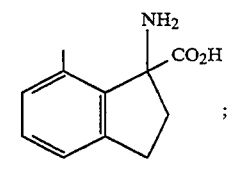

$R^1$ is $C_1$–$C_6$ linear or branched chain alkyl or cyclopropyl;

$R^2$ is unsubstituted or substituted phenyl where the substituent is fluoro, chloro, bromo, iodo, nitro, carboxy, hydroxy, amino, hydroxy $C_1$–$C_4$-alkyl, $C_1$–$C_4$-mono or di-alkyl amino; or cyclohexyl;

or the optical isomers, prodrugs or pharmaceutically acceptable salts thereof.

The preferred compounds of this invention as set forth in the Examples are as follows:

1. N-{(3R)-1,3-Dihydro-1-methyl-2-oxo-5-phenyl-1H-1,4-benzodiazepin-3-yl}-N'-{[3-((2S)-tertbutyloxycarbonylamino-2-methoxycarbonyl) ethylphenyl]urea}, 2. N-{(3R)-1,3-Dihydro-1-methyl-2-oxo-5-phenyl-1H-1,4-benzodiazepin-3-yl}-{[3-((2S)-aminomethoxycarbonyl)ethylphenyl]-urea}, 3. N-{(3R)-1,3-Dihydro-1-methyl-2-oxo-5-phenyl-1H-1,4-benzodiazepin-3-yl}-N'-{[3-((2S)-amino-2-carboxy)ethylphenyl]-urea}, 4. N-{(3R)-1, 3-Dihydro-1-methyl-2-oxo-5-cyclohexyl-1H-1,4-benzodiazepin-3-yl}-N'-{[3-((2S)-tertbutyloxycarbonylamino-2-methoxycarbonyl)ethylphenyl]-urea}, 5. N-{(3R )-1,3-Dihydro-1-methyl-2-oxo-5-cyclohexyl-1H-1,4-benzodiazepin-3-yl }-N'-{[3-((2S)-amino-2methoxycarbonyl)ethylphenyl]-urea}, 6. N-{(3R)-1,3-Dihydro-1-methyl-2-oxo-5-cyclohexyl-1H-1,4-benzodiazepin-3-yl}-N'-{[3-((2S)-amino-2-carboxy)ethylphenyl]-urea}, 7. N-{(3R)-1,3-Dihydro-1-methyl-2-oxo-5-phenyl-1H-1,4-benzodiazepin-3-yl}-N'-{[3-((1S)-tertbutyloxycarbonylamino-1-methoxycarbonyl)methylphenyl]-urea},
8. N-{(3R)-1,3-Dihydro-1-methyl-2-oxo-5-phenyl-1H-1,4-benzodiazepin-3-yl}-N'-{[3-((1S)-amino-1methoxycarbonyl)methylphenyl]-urea},
9. N-{(3R)-1,3-Dihydro-1-methyl-2-oxo-5-phenyl-1H-1,4-benzodiazepin-3-yl}-N'-{[3-((1S)-amino-1-carboxy)methylphenyl]-urea},
10. N-{(3R)-1,3-Dihydro-1-methyl-2-oxo-5-phenyl-1H-1,4-benzodiazepin-3-yl}-N'-{[3-((1R)-amino-1-carboxy)methylphenyl]-urea},
11. N-{(3R)-1,3-Dihydro-1-methyl-2-oxo-5-phenyl-1H-1,4-benzodiazepin-3-yl}-N'-{[3-((1R, S)-tertbutyloxycarbonylamino-2-methoxycarbonyl)ethylphenyl]-urea},
12. N-{(3R)-1,3-Dihydro-1-methyl-2-oxo-5-phenyl-1H-1,4-benzodiazepin-3-yl}-N'-{[3-((1R, S)-amino-2methoxycarbonyl)ethylphenyl]-urea},
13. N-{(3R)-1,3-Dihydro-1-methyl-2-oxo-5-phenyl-1H-1,4-benzodiazepin-3-yl}-N'-{[3-((1R, S)-amino-2carboxy)ethylphenyl]-urea},
14. N-{(3R)-1,3-Dihydro-1-methyl-2-oxo-5-phenyl-1H-1,4-benzodiazepin-3-yl}-N'-{[8-(methyl-2-(R, S)tert-butyloxycarbonylamino-1,2,3,4-tetrahydro-2-naphthoate)]-urea},
15. N-{(3R)-1,3-Dihydro-1-methyl-2-oxo-5-phenyl-1H-1,4-benzodiazepin-3-yl}-N'-{[7-(methyl-2-(R, S)tert-butyloxycarbonylamino-1,2,3,4-tetrahydro-2-naphthoate)]-urea},
16. N-{(3R)-1,3-Dihydro-1-methyl-2-oxo-5-phenyl-1H-1,4-benzodiazepin-3-yl}-N'-{[7-(methyl-2-(R, S)amino-1,2,3,4-tetrahydro-2-naphthoate)]-urea},
17. N-{(3R)-1,3-Dihydro-1-methyl-2-oxo-5-phenyl-1H-1,4-benzodiazepin-3-yl}-N'-{[7-(2-(R, S)-amino-1,2,3,4-tetrahydro-2-naphthoic acid)]-urea},
18. N-{(3R)-1,3-Dihydro-1-methyl-2-oxo-5-phenyl-1H-1,4-benzodiazepin-3-yl}-N'-{[6-(methyl-2-(R, S)tert-butyloxycarbonylamino-1,2,3,4-tetrahydronaphthoate)]-urea},
19. N-{(3R)-1,3-Dihydro-1-methyl-2-oxo-5-phenyl-1H-1,4-benzodiazepin-3-yl}-N'-{[6-(methyl-2-(R, S)amino-1,2,3,4-tetrahydro-2-naphthoate)]-urea},
20. N-{(3R)-1,3-Dihydro-1-methyl-2-oxo-5-phenyl-1H-1,4-benzodiazepin-3-yl}-N'-{[6-(2-(R,S)-amino-1,2,3,4-tetrahydro-2-naphthoic acid)]-urea},
21. N-{(3R)-1,3-Dihydro-1-methyl-2-oxo-5-phenyl-1H-1,4-benzodiazepin-3-yl}-N'-{[5-(methyl-2-(R,S)tert-butyloxycarbonylamino-1,2,3,4-tetrahydro-2-naphthoate)]-urea},
22. N-{(3R)-1,3-Dihydro-1-methyl-2-oxo-5-phenyl-1H-1,4-benzodiazepin-3-yl}-N'-{[5-(methyl-2-(R, S)amino-1,2,3,4-tetrahydro-2-naphthoate)]-urea}, or
23. N-{(3R)-1,3-Dihydro-1-methyl-2-oxo-5-phenyl-1H-1,4-benzodiazepin-3-yl}-N'-{[5-(2-(R,S)-amino-1,2,3,4-tetrahydro-2-naphthoic acid)]-urea}, or the pharmaceutically acceptable salts thereof.

The most preferred compounds of this invention as set forth in the Examples are as follows:

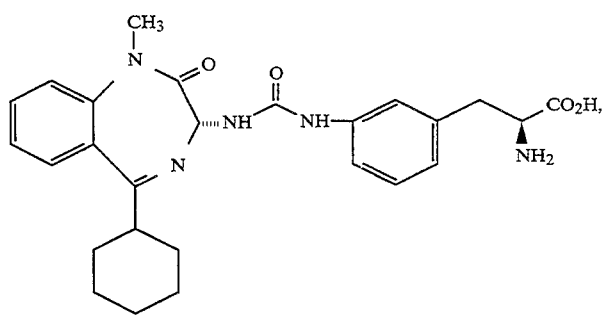

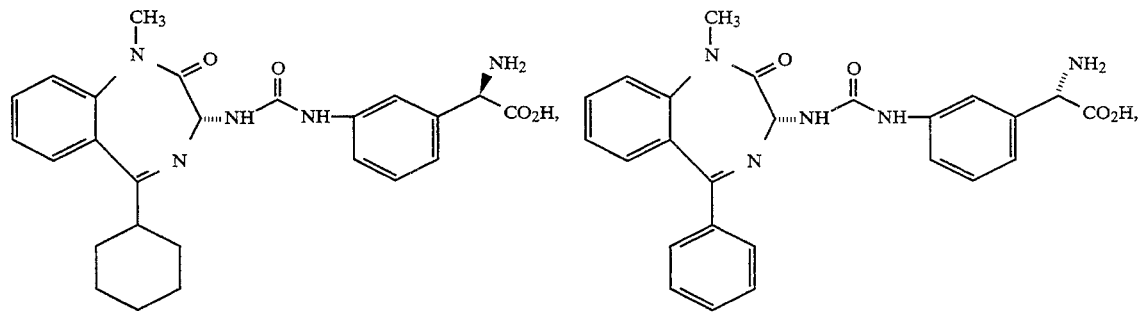

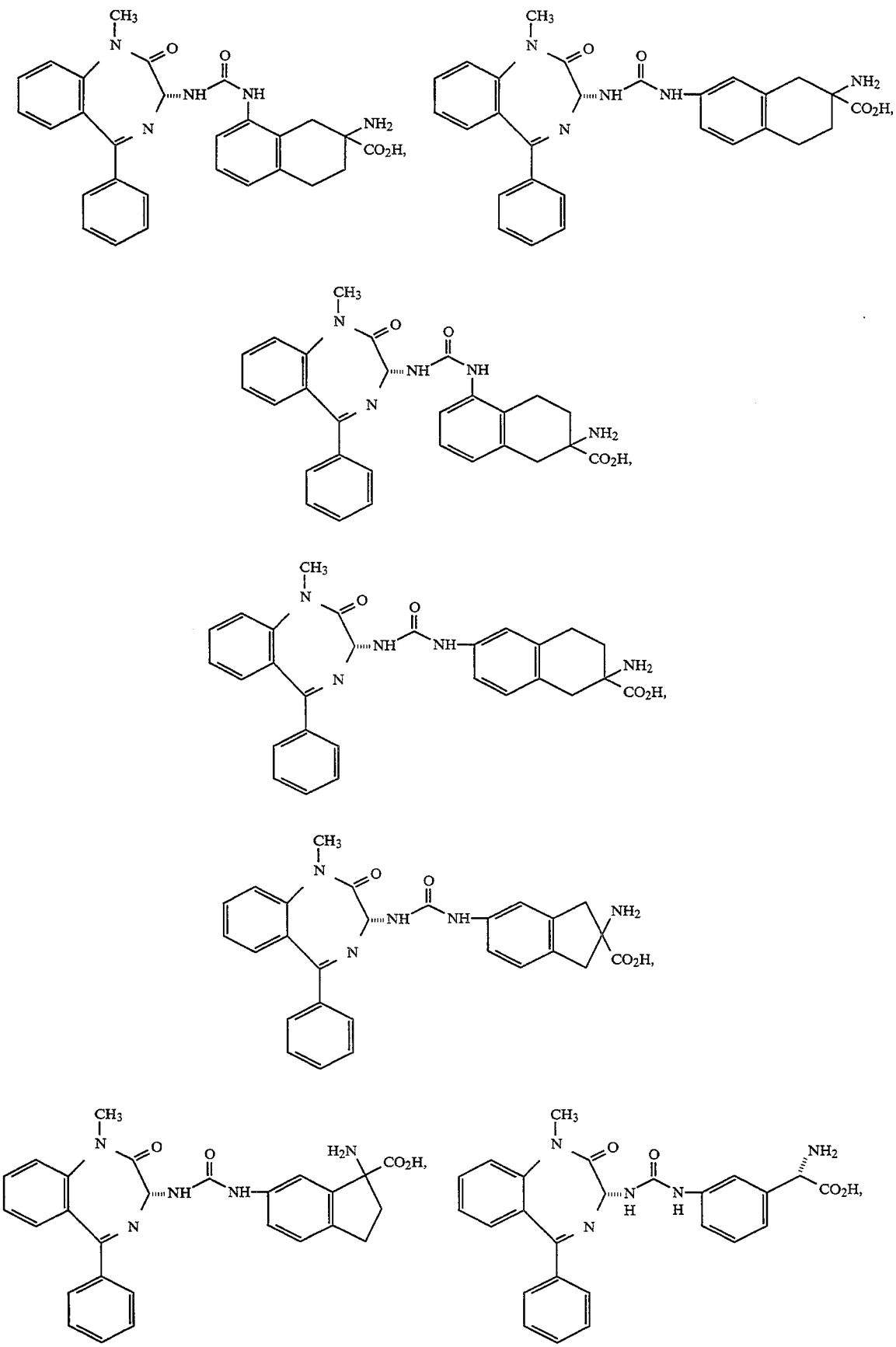

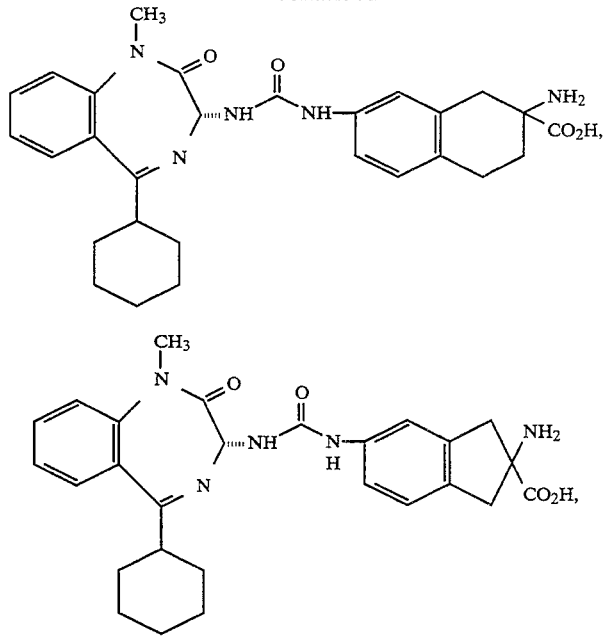

or the pharmaceutically acceptable salts thereof.

It will be appreciated that formula (I) is intended to embrace all possible isomers, including optical isomers, and mixtures thereof, including racemates.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bungaard, Elsevier, .1985.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I by conventional chemical methods. Generally, the salts are prepared by reacting the Formula I compound with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating compounds of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I antagonize CCK and/or gastrin and are useful as pharmaceutical agents for animals, preferably for mammals, and most especially for humans, for the treatment and prevention of gastrointestinal disorders and central nervous system disorders.

Examples of such gastrointestinal disorders include ulcers, such as peptic and gastrointestinal ulcers, irritable bowel syndrome, gastroesophagenal reflux disease or excess pancreatic or gastrin secretion, acute pancreatitis, or motility disorders, Zollinger-Ellison syndrome, and antral and cell hyperplasia.

Examples of central nervous system disorders include central nervous system disorders caused by CCK interaction with dopamine, such as neuroleptic induced tardive dyskinesia, Parkinson's disease, schizophrenia, other psychosis or Gilles de la Tourerrs syndrome, and disorders of appetite regulatory systems.

The compounds of Formula I may further be useful in the treatment or prevention of additional central nervous system disorders including neurological and psychiatric disorders. Examples of such central nervous system disorders include anxiety disorders and panic disorders, wherein CCK and/or gastrin is involved. Additional examples of central nervous system disorders include panic syndrome, anticipatory anxiety, phobic anxiety, panic anxiety, chronic anxiety, and endogeneous anxiety.

The compounds of Formula I may further be useful in the treatment of oncologic disorders wherein CCK or gastrin may be involved. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The compounds of Formula I may further be used to control pupil constriction in the eye. The compounds may be used for therapeutic purposes during eye examinations and intraocular surgery in order to prevent miosis. The compounds may further be used to inhibit miosis occurring in association with iritis, uveitis and trauma.

The compounds of Formula I are also useful for directly inducing analgesia, opiate or non-opiate mediated, as well as anesthesia or loss of the sensation of pain.

The compounds of Formula I may further be useful for preventing or treating the withdrawal response produced by chronic treatment or abuse of drugs or alcohol. Such drugs include, but are not limited to, cocaine, alcohol or nicotine.

The compounds of Formula I are also useful for directly inducing analgesia, opiade or non-opiade mediated, as well as anesthesia or loss of the sensation of pain.

The compounds of formula (I) may also be useful as neuroprotective agents, for example, in the treatment and/or prevention of neurodegenerative disorders arising as a consequence of such pathological conditions as stroke, hypoglycaemia, cerebal palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-pontocerebellar atrophy, anoxia such as from drowning, spinal cord and head injury, and poisoning by neurotoxins, including environmental neurotoxins.

The compounds of Formula I may also be useful in the treatment of depression. Depression can be the result of organic disease, secondary to stress associated with personal loss, or idiopathic in origin. There is a strong tendency for familial occurrence in some forms of depression suggesting a mechanistic cause for at least some forms of depression. The diagnosis of depression is made primarily by quantification of alterations in a patients' mood. These evaluations of mood are generally performed by a physician or quantified by a neuropsychologist using validated rating scales such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of .worthlessness, and guilt. The standards for diagnosis of depression as well as all psychiatric diagnoses are collected in the diagnostic and Statistical Manual of Mental Disorders (Third Edition Revised) referred to as the DSM-III-R manual published by the American Psychiatric Association, 1987.

The present invention also encompasses a pharmaceutical composition useful in the treatment of CCK and/or gastrin disorders comprising the administration of a therapeutically effective but non-toxic amount of the compounds of Formula I, with or without pharmaceutically acceptable carriers or diluents.

The compounds of Formula I, may be administered to animals, preferably to mammals, and most especially to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight, administered in single or divided doses.

In the effective treatment of panic syndrome, panic disorder, anxiety disorder and the like, preferably about 0.05 mg/kg to about 1.0 mg/kg of CCK antagonist may be administered orally (p.o.), administered in single or divided doses per day (b.i.d.). Other routes of administration are also suitable.

For directly inducing analgesia, anesthesia or loss of pain sensation, the effective dosage range is preferably from about 100 ng/kg to about 1 mg/kg by intraperitoneal administration. Oral administration is an alternative route, as well as others.

In the treatment of irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumor palliative for gastrointestinal neoplasma with gastrin receptors, as a modulator of central nervous activity, treatment of Zollinger–Ellison snydrome, or in the treatment of peptic ulcer disease, an effective dosage is preferably from about 0.1 to about 10 mg/kg, administered one-to-four times daily is indicated.

Because these compounds antagonize the function of CCK in animals, they may also be used as feed additives to increase the food intake of animals in daily dosage preferably from about 0.05 mg/kg to about 50 mg/kg of body weight.

The compounds of Formula I may be prepared according to the reaction schemes as set forth below.

5,378,838
SCHEME 1
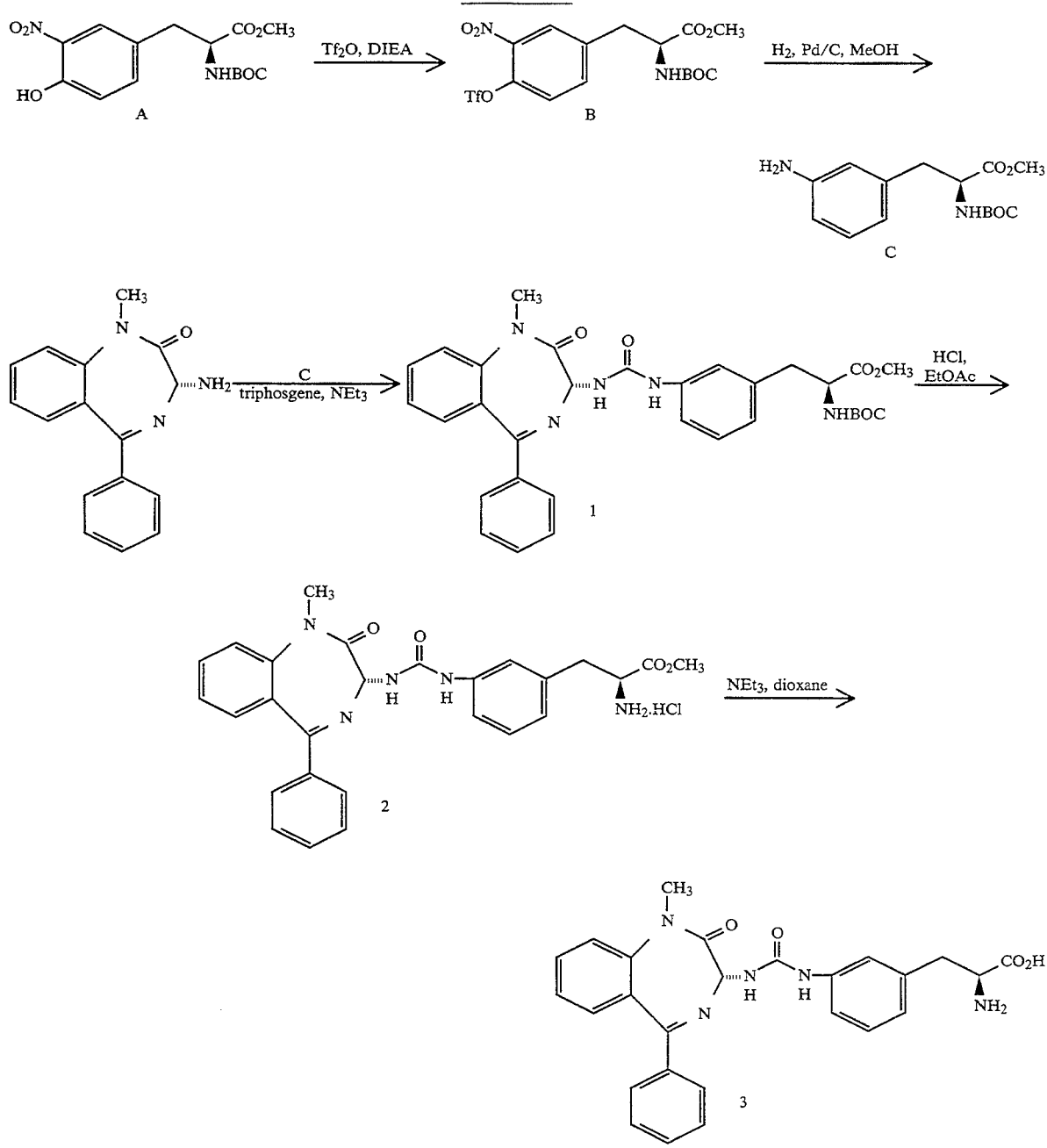
SCHEME 2
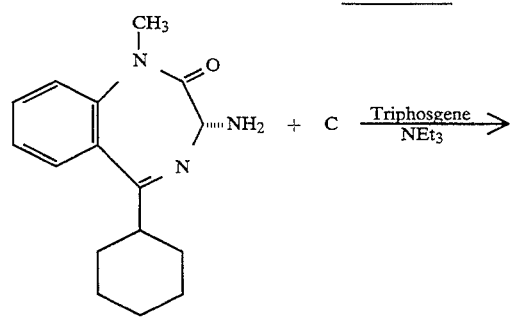

SCHEME 2
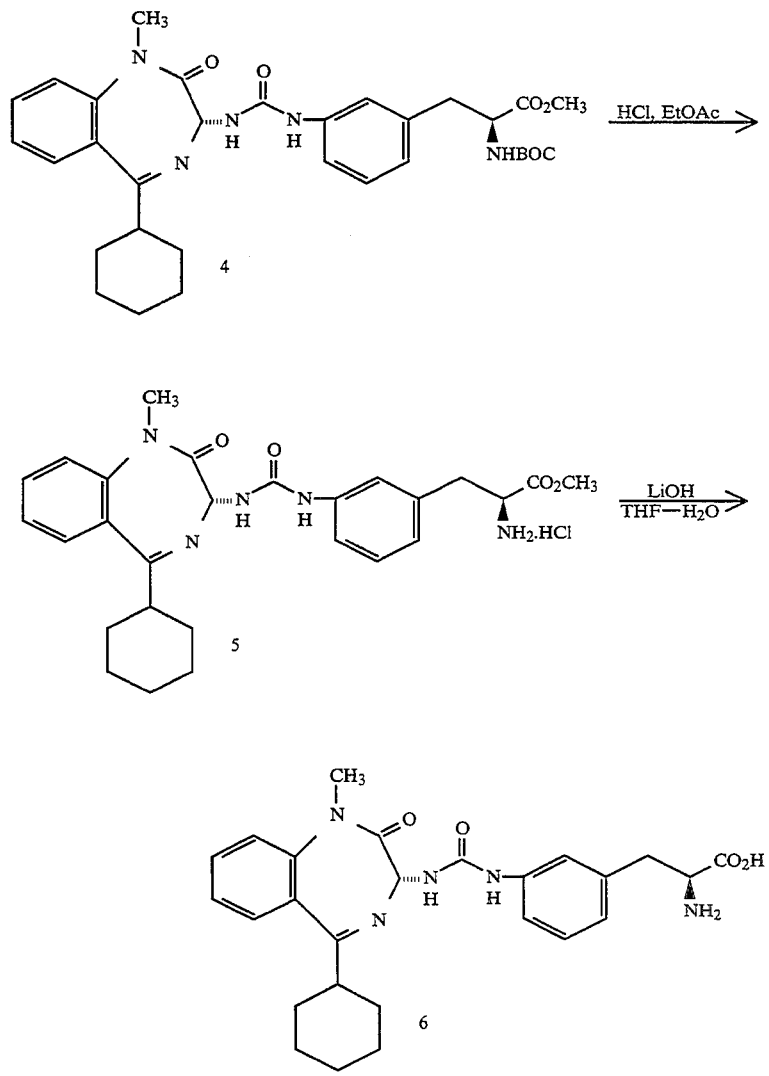
SCHEME 3
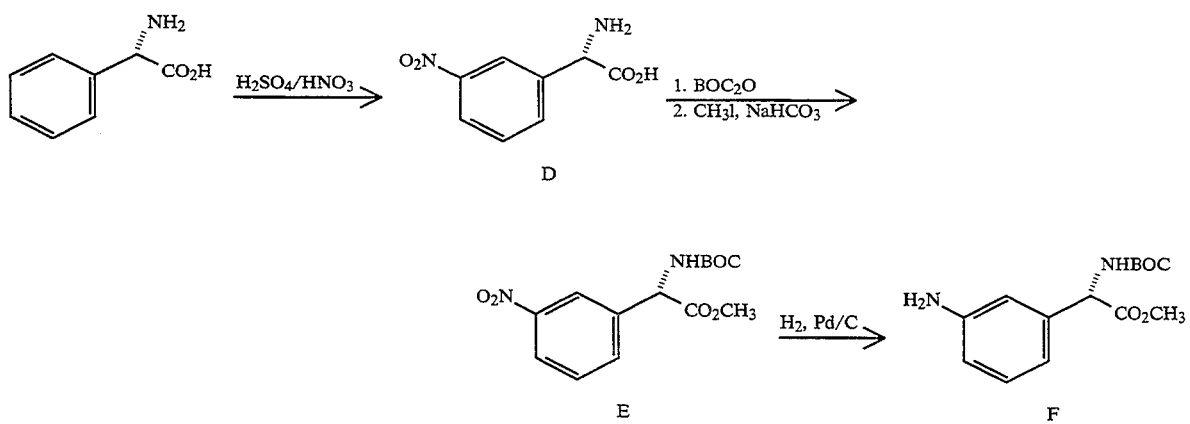

-continued
SCHEME 3
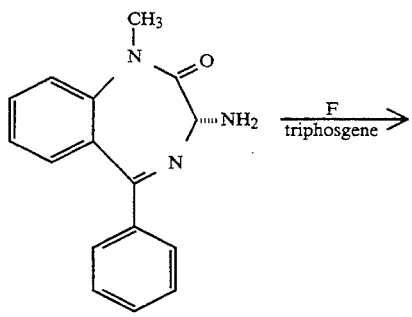
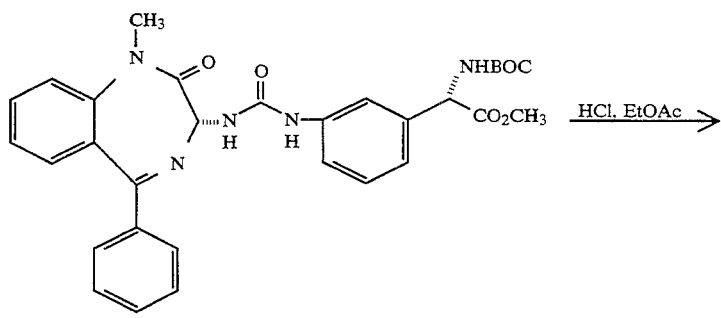
7
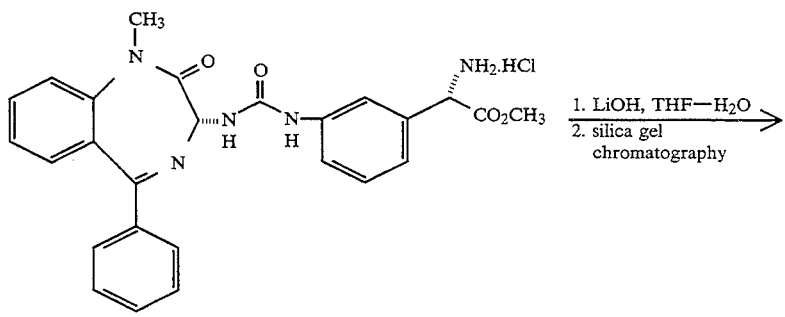
8
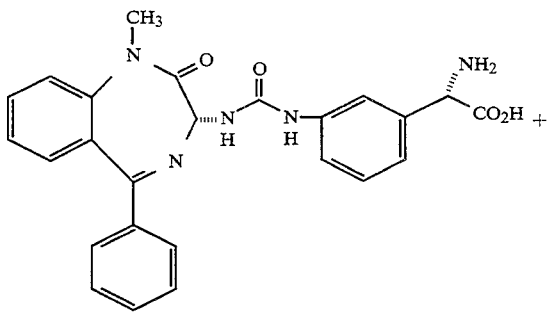
9

5,378,838
-continued
SCHEME 3
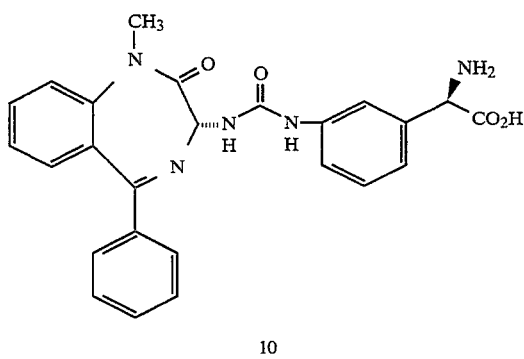
SCHEME 4
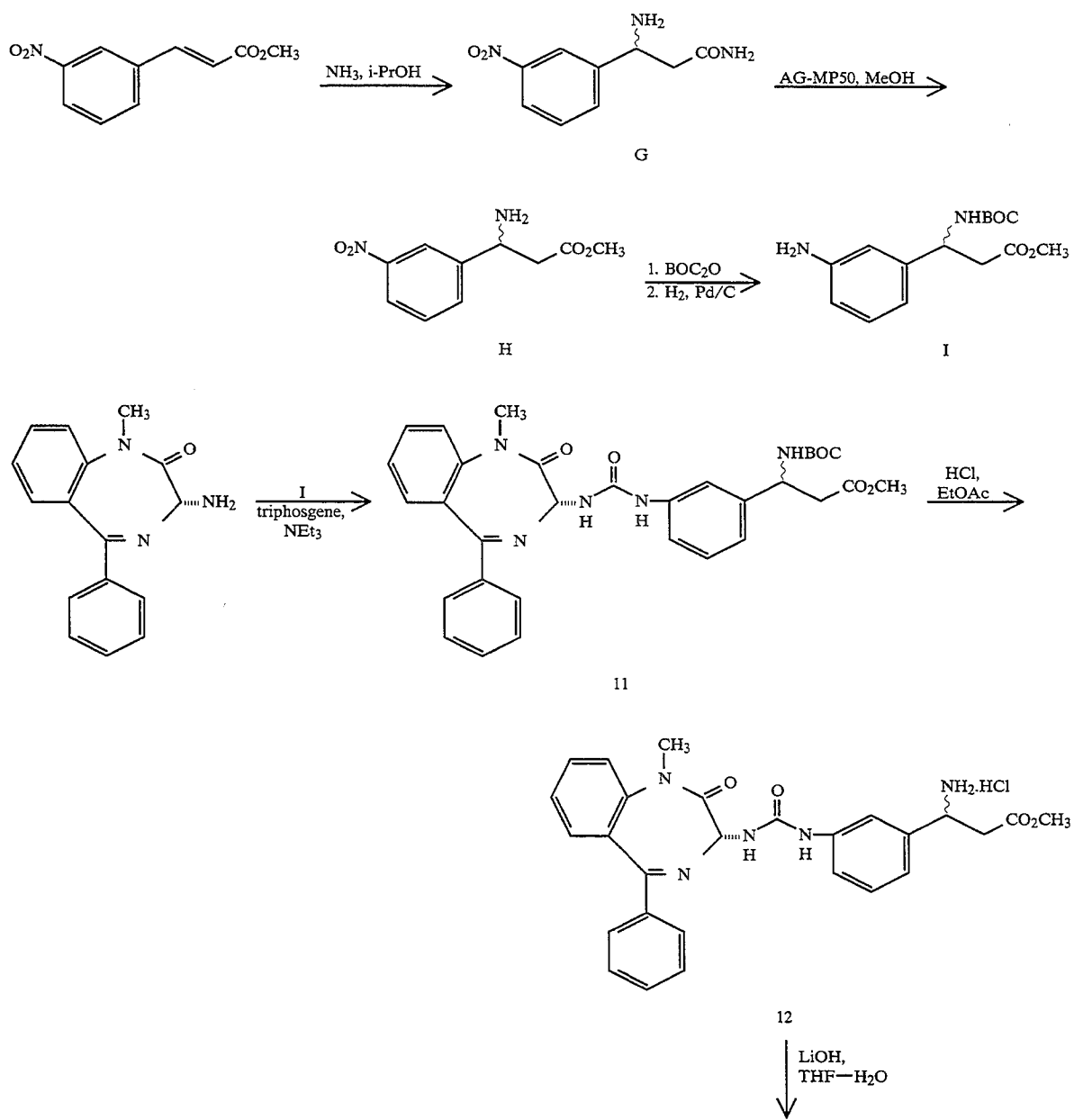

-continued
SCHEME 4
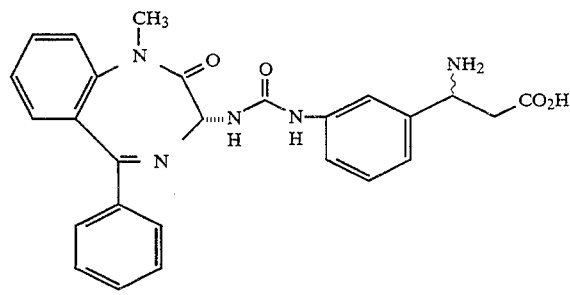
SCHEME 5
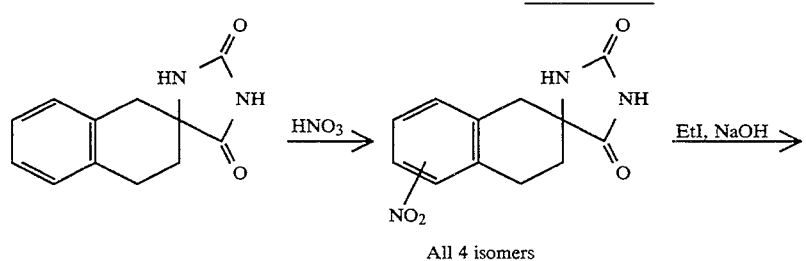
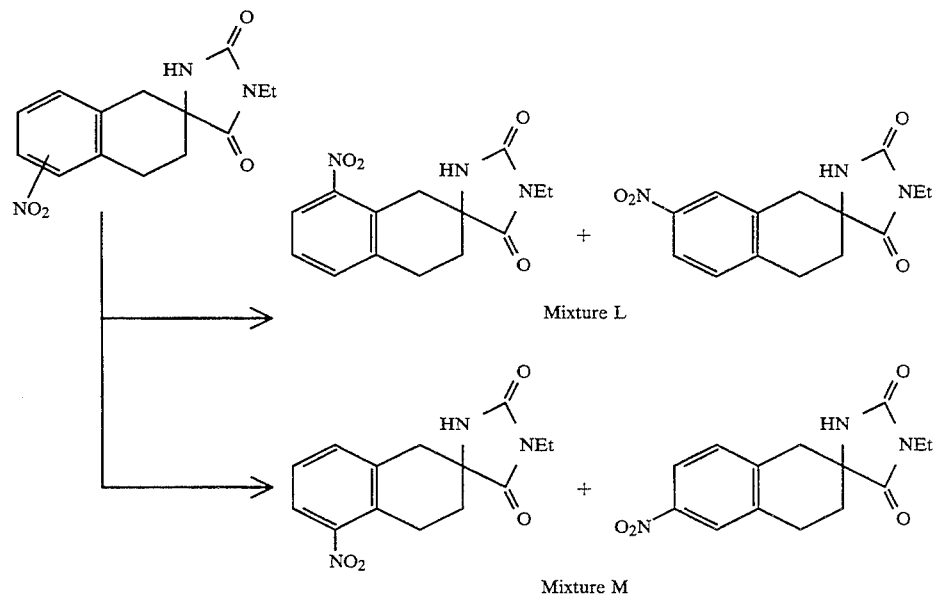
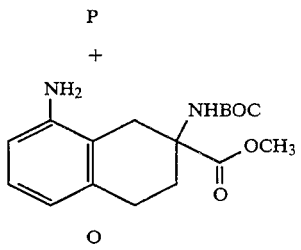
Mixture L 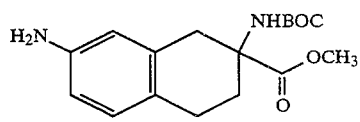

-continued
SCHEME 5
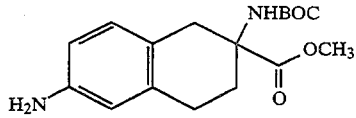
Q
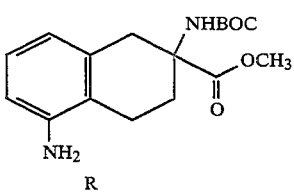
R
Mixture M  →  1. HCl, reflux
2. BOC₂O
3. CH₃I, NaHCO₃, DMF
4. H₂, Pd/C
5. Separate isomers
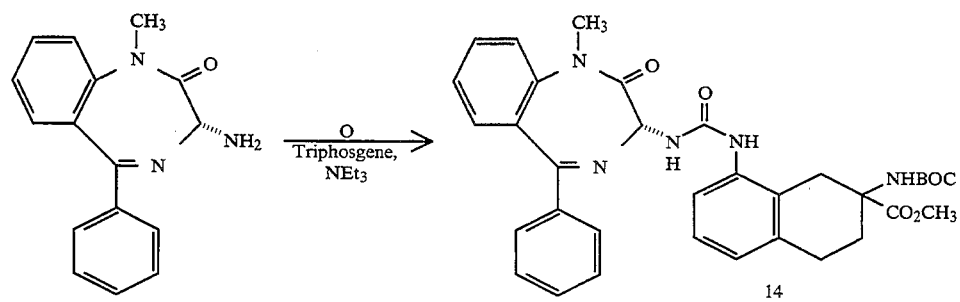
14
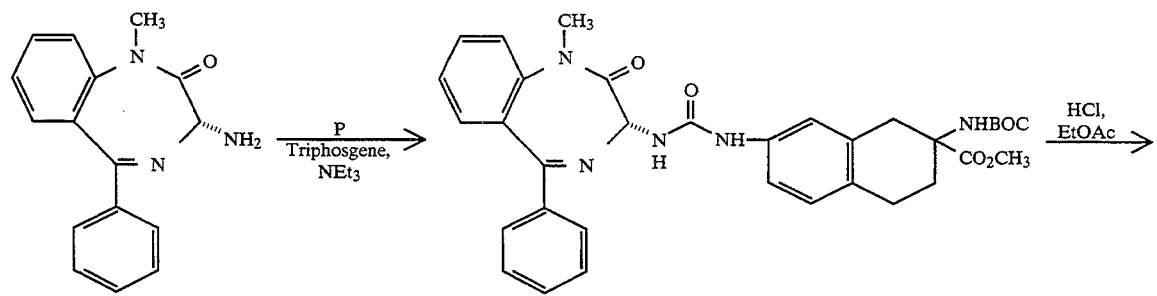
15
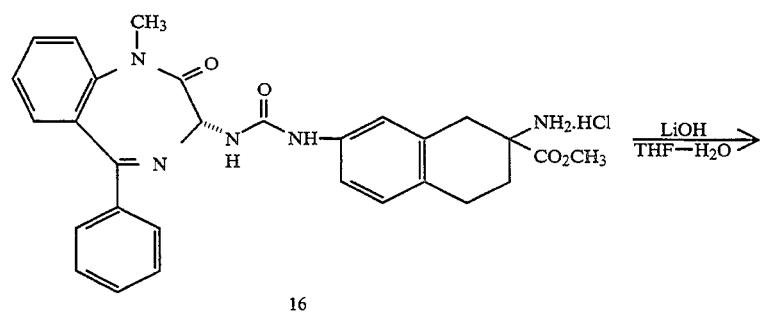
16
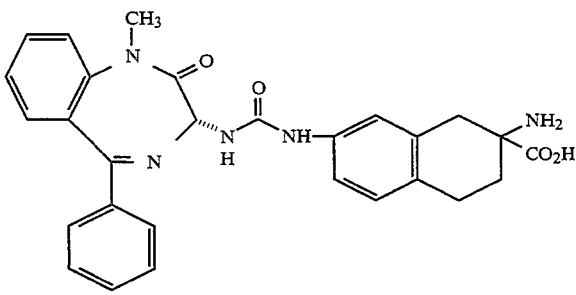
17

-continued
SCHEME 5
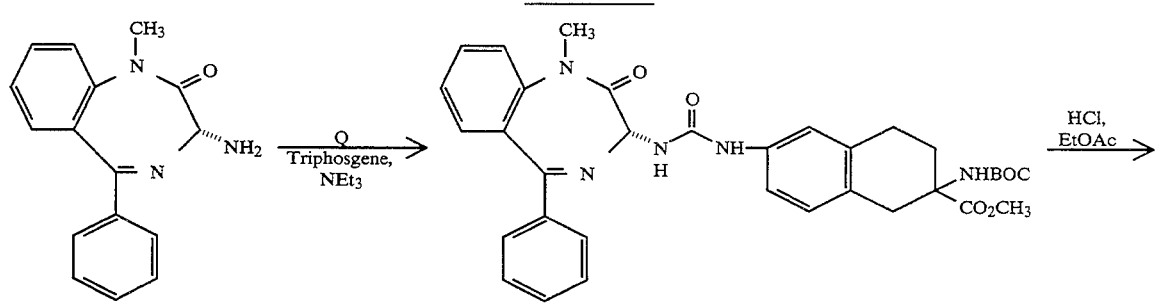
18
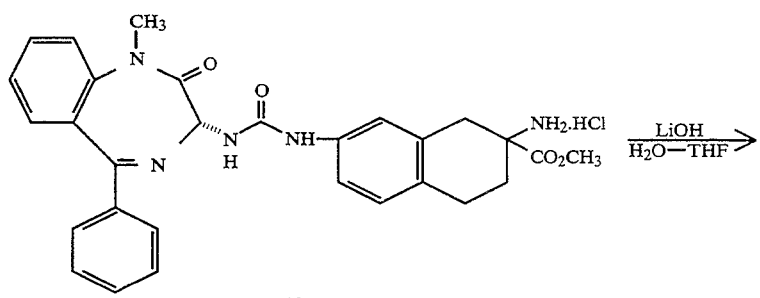
19
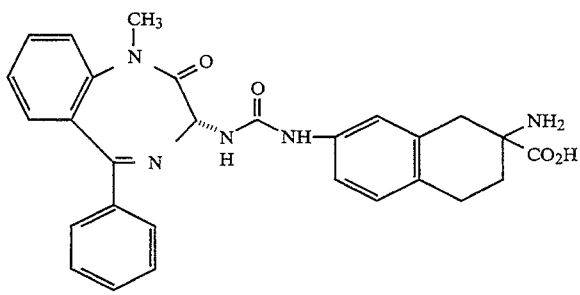
20
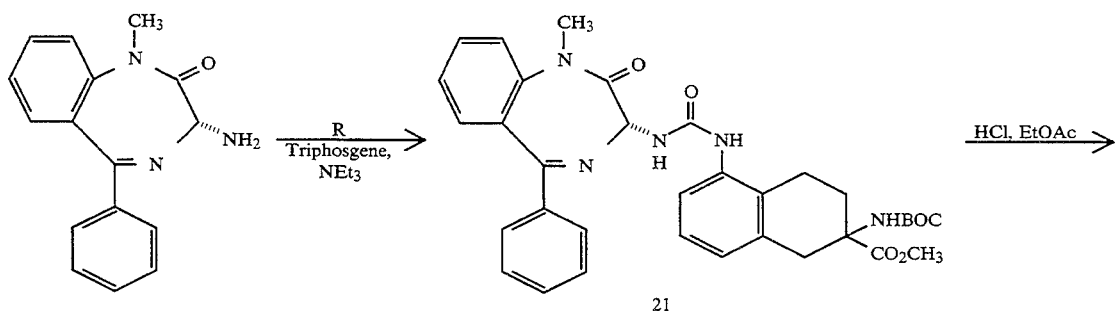
21
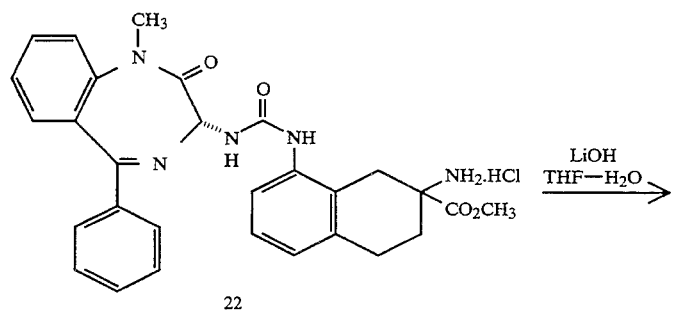
22

SCHEME 5 -continued

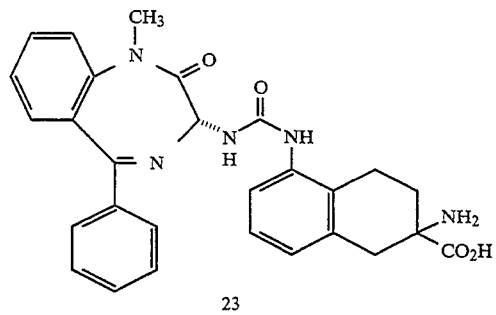

23

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM Hepes buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM Hepes, 1 mM EGTA, 5 mM $MgCl_2$, 150 mM NaCl, bacitracin 0.25 mg/ml, soya bean trypsin inhibitor 0.1 mg/ml, and bovine serum albumin 2 mg/ml, pH 6.5 at 25° C.) using a teflon homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabeled CCK-8 sulfated to give a final concentration of 1 μM (for nonspecific binding) or the compounds of Formula I (for determination of inhibition of $^{125}$I-CCK binding) and 50 μl of 500 pM $^{125}$I-CCK-8 (i.e. 50 pM final concentration) Were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 mM NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The $P_2$ pellet was resuspended in binding assay buffer (20 mM N-2-hydroxyethyl-piperazine-N'-2-ethane sulfonic acid (HEPES), 5 mM $MgCl_2$, 0.25 mg/ml bacitracin, 1 mM ethylene glycol-bis-(B-aminoethylether-N,N'-tetraacetic acid) (EGTA)pH 6.5 at 25° C., using a teflon homogenizer (5 strokes at 500 rpm) to give a final concentration of 10 mg original wet weight 11.2 mls buffer. For the binding assay, 50 μl of buffer (for total binding) or unlabeled CCK-8 sulfate to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated on Whatman GF/C filters by rapid filtration (Brandell 24 well cell Harvester) with 3×5 ml washes of cold 100 mM NaCl. The radioactivity on the filters was then counted with a LKB gamma counter.

5. Gastrin Antagonism

Gastrin antagonist activity of compounds of Formula I is determined using the following assay.

A. Gastrin Receptor Binding in Guinea Pig Gastric Glands

Preparation of guinea pig gastric mucosal glands

Guinea pig gastric mucosal glands were prepared by the procedure of Chang et al., Science 230, 177–179 (1985) with slight modification. Gastric mucosa from guinea pigs (300–500 g body weight, male Hartley) were isolated by scraping with a glass slide after washing stomachs in ice-cold, aerated buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 50 mM HEPES, 0.25 mg/ml bacitracin, 0.10 mg/ml soya bean trypsin inhibitor, 0.1 mg/ml bovine serum albumin, at pH 6.5, and then incubated in a 37° C. shaking water bath for 40 minutes in buffer containing 1 mg/ml collagenase and bubbled with 95% $O_2$ and 5% $CO_2$. The tissues were passed twice through a 5 ml syringe to liberate the gastric glands, and then filtered through Nitex #202 gauge nylon mesh. The filtered glands were centrifuged at 272 g for 5 minutes and washed twice by resuspension in 25 ml buffer and centrifugation.

B. Binding Studies

The washed guinea pig gastric glands prepared as above were resuspended in 25 ml of standard buffer. For binding studies, to 250 μl of gastric glands, 30 μl of buffer (for total binding) or gastrin (3 μM final concentration, for nonspecific binding) or test compound and 20 μl of $^{125}$I-gastrin (NEN, 2200 Ci/mmole, 0.1 nM final concentration) were added. AV assays were run in triplicate. The tubes were aerated with 95% $O_2$ and 5% $CO_2$ and capped. The reaction mixtures after incubation at 25° C. for 30 minutes in a shaking water bath were rapidly filtered (Brandell 24 well cell harvester) over Whatman and G/F B filters presoaked in assay buffer and immediately washed further with 3×4 ml of 100mM ice cold NaCl. The radioactivity on the filters was measured using a LKB gamma counter.

In Vitro Results

Effect of The Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μm CCK) binding.

Drug displacement studies were performed with at least 10 concentrations of compounds of formula 1 and the IC$_{50}$ values were determined by regression analysis. IC$_{50}$ refers to the concentration of the compound required to inhibit 50% of specific binding of $^{125}$I-CCK-8.

The data in Table I were obtained for compounds of Formula I.

TABLE I

| Compound of Example | CCK RECEPTOR BINDING RESULTS IC$_{50}$ (μM) | |
| --- | --- | --- |
| | $^{125}$I-CCK Pancreas | $^{125}$I-CCK Brain |
| 1. | >3 | 0.0296 |
| 2. | >>3 | 0.114 |
| 3. | >>3 | 0.0613 |
| 4. | 0.961 | 0.0039 |
| 5. | 0.924 | 0.0092 |
| 6. | 1.786 | 0.0011 |
| 7. | >>3 | 1.98 |
| 8. | >>3 | 0.958 |
| 9. | >3 | 1.33 |
| 10. | >>3 | 3.59 |
| 11. | >3 | 0.386 |
| 12. | >>3 | >3 |
| 13. | >3 | >3 |
| 14. | >3 | 0.647 |
| 15. | >3 | 0.126 |
| 16. | >3 | 0.148 |
| 17. | >3 | 0.0284 |
| 18. | >>3 | >3 |
| 19. | >3 | >3 |
| 20. | >3 | 3.52 |
| 21. | >3 | 1.69 |
| 22. | >3 | 2.16 |
| 23. | >>3 | >3 |

EXAMPLES

Examples provided are intended to assist in a further understanding of the invention. Particular materials employed, species and conditions are intended to be further illustrative of the invention and not limitative of the reasonable scope thereof.

EXAMPLE 1

Synthesis of N-{(3R)-1,3-Dihydro-1-methyl-2-oxo-5-phenyl-1H-1,4-benzodiazepin-3-yl}-N'-{[3-((2S)-tertbutyloxycarbonylamino-2-methoxycarbonyl)ethylphenyl]urea}

Part 1: Methyl 3-(4-Triflyl-3-nitrophenyl)-2(S)-tert-butyloxy carbonyl-aminopropionate (B)

To an ice cold solution of 25 ml of methylene chloride under nitrogen containing 3 g of 3-(4-hydroxy-3-nitrophenyl)-N$^\alpha$-Boc-L-alanine methyl ester A and 1.61 ml of diisopropylethylamine was added 1.55 ml of triflic anhydride over a 20 minute period. The reaction mixture was stirred at 0° C. for 30 minutes more and then was concentrated under reduced pressure. The residual material was plug-filtered through silica gel using ethyl acetate-hexane (1:1 v/v) as eluant. The title compound was obtained as a solid (1.624 g).

Part 2: Methyl 3-(3-Aminophenyl)-2(S)-tertbutyloxycarbonylaminopropionate (C)

Methyl 3-(4-triflyl-3-nitrophenyl)-2(S)-tertbutyloxycarbonylaminopropionate (730 mg), diisopropylethylamine (295 mL) and 365 mg of 10% palladium/carbon catalyst were combined in 50 mL of methanol and hydrogenated on a Parr apparatus at 55 p.s.i. for 60 minutes. The reaction mixture was filtered and concentrated. The residue was dissolved in a minimum amount of chloroform and applied to a silica gel column; flash chromatography (hexane-ethyl acetate elution 1:1, v/v) afforded 346 mg of the title compound.

Part 3.: N-{(3R)-1,3-Dihydro-1-methyl-2-oxo-5-phenyl-1H-1,4-benzodiazepin-3-yl}-N'-{[3-((2S)tert-butyloxycarbonylamino-2-methoxycarbonyl)ethylphenyl]urea}

A solution of methyl 3-(3-aminophenyl)-2(S)tert-butyloxycarbonylaminopropionate(C) (332 mg) in 30 mL of tetrahydrofuran was stirred magnetically in an ice bath under a nitrogen atmosphere and treated in sequence with triethylamine (472 mL) and triphosgene (112 mg) under anhydrous conditions. The pH of the reaction mixture was adjusted to approximately 8 with the incremental addition of triethylamine. The reaction mixture was warmed to room temperature for 10 minutes and recooled to 0° C. A solution of 10 mL of tetrahydrofuran containing 270 mg of 1,3-dihydro-1-methyl-3(R)-amino-5-phenyl-2H-1,4-benzodiazepin-2- one was then added dropwise over a five minute period. The reaction mixture was stirred fifteen minutes more and was then partitioned between ethyl acetate–10% citric acid solution. The aqueous layer was extracted with ethyl acetate and the combined organic extracts were washed with brine, dried (sodium sulfate), and rotoevaporated. Flash chromatography of the crude reaction product on silica gel (ethyl acetate-hexane elution, 3:2 v/v) afforded the title compound (534mg) as a solid: m.p. 135°–138° C. (d).

HPLC=>99% pure at 214 nm; TLC R$_f$=0.58 (CH$_2$Cl$_2$—CH$_3$OH—HOAc—H$_2$O, 90:10:1:1). NMR(CDCl$_3$): Consistent with structure assignment and confirms presence of solvent. FAB MS: 586 (M$^+$+1). Analysis for C$_{32}$H$_{35}$N$_5$O$_6$•0.15H$_2$O•0.55EtOAc: Calculated: C, 64.50; H, 6.28; N, 11.00. Found: C, 64.47; H, 6.30; N, 11.00.

EXAMPLE 2

Synthesis of N-{(3R)-1,3-Dihydro-1-methyl-2-oxo-5-phenyl-1H-1,4-benzodiazepin-3-yl}-N'-{[3-((2S)-amino-2-methoxycarbonyl)ethylphenyl]-urea}

A solution of 350 mg of N-{(3R)-1,3-dihydro-1-methyl-2-oxo-5-phenyl-1H-1,4-benzodiazepin-3-yl}-N,-{[3-((2S)-tert-butyloxycarbonylamino-2-methoxxcarbonyl)ethylphenyl]-urea}in 15 mL of ethyl acetate was cooled to 0° C. under nitrogen. A steady stream of hydrogen chloride gas was passed through the reaction mixture for 10 minutes during which time a precipitate was formed. The reaction vessel was sealed and the reaction mixture was stirred for an additional 30 minutes. All volatiles were removed under reduced pressure and the residual material was chromatographed on silica gel (chloroform:methanol:concentrated ammonium hydroxide, 90:10:1 v/v) to give 284 mg of the title compound as a solid: m.p. 127°–129° C. (d). HPLC=99% pure at 214 rim; TLC $R_f$=0.23 ($CH_2Cl_2$—$CH_3OH$—HOAc—$H_2O$, 90:10:1:1). NMR(DMSO-$d_6$): Consistent with structure assignment and confirms presence of solvent. FAB MS: 486 (M+ +1). Analysis for $C_{27}H_{27}N_5O_4$•0.7$CHCl_3$•0.2$CH_3OH$: Calculated: C, 58.23; H, 4.99; N, 12.17. Found: C, 58.25; H, 4.94; N, 12.15.

EXAMPLE 3

Synthesis of
N-{(3R)-1,3-Dihydro-1-methyl-2-oxo-5-phenyl-1H-1,4-benzodiazepin-3-yl}-N'-{[3-((2S)-amino-2-carboxy)ethylphenyl]-urea}

Triethylamine (63 mL) and 217 mg of N-{(3R)-1,3-dihydro-1-methyl-2-oxo-5-phenyl-1H-1,4-benzodiazepin-3-yl}-N'-{[3-((2S)-amino-2-methoxycarbonyl)ethylphenyl]-urea} were combined in a dioxane-water mixture (2:1, v/v) and stirred at room temperature. The progress of the reaction was monitored by HPLC. After 11 days the solvent was roto-evaporated and the crude product was purified by preparative thick layer chromatography on pre-coated silica gel plates (1 mm thickness, $CHCl_3$—$CH_3OH$—HOAc—$H_2O$, 90:10:1:1). The product was extracted from the silica gel with chloroform-methanol (88:12 v/v) to give 72 mg of the title compound as its triethylamine salt. This material was further worked-up by preparative reverse phase HPLC (Vydac C-18 column, acetonitrile-water (containing 0.01% trifluoroacetic acid), 8 mL/min flow rate, 45 minute gradient) to yield, after lyophilization, 59 mg of the title compound as a solid: m.p. 195° C. (d). HPLC=99% pure at 214 nm; TLC $R_f$=0.44 (EtOAc-pyridine—HOAc—$H_2O$, 10:5:1:3). NMR(DMSO-$d_6$): Consistent with structure assignment and confirms presence of solvent. FAB MS: 472 (M+ +1). Analysis for $C_{25}H_{25}N_5O_4$•1.6 TFA•1.0 $H_2O$: Calculated: C, 52.17; H, 4.29; N, 10.42. Found: C, 52.15; H, 4.25; N, 10.47.

EXAMPLE 4

N-{(3R)-1,3-Dihydro-1-methyl-2-oxo-5-cyclohexyl-1H-1,4-benzodiazepin-3-yl}-N'-{[3-((2S)-tert-butyloxycarbonylamino-2-methoxycarbonyl)ethylphenyl]-urea}.

A solution of methyl 3-(3-aminophenyl)-2-(S)-tert-butyloxycarbonylaminopropionate(C) (108 mg) in 10 mL of tetrahydrofuran was stirred magnetically in an ice bath under a nitrogen atmosphere and treated in sequence with triethylamine (155 mL) and triphosgene (37 mg) under anhydrous conditions. The pH of the reaction mixture was adjusted to approximately 8 with the incremental addition of triethylamine. The reaction mixture was stirred for minutes at 0° C. warmed to room temperature for 8 minutes and recooled to 0° C. A solution of 3 mL of tetrahydrofuran containing 100 mg of 1,3-dihydro-1-methyl-3(R)-amino-5-cyclohexyl-2H-1,4-benzo-diazepin-2-one was then added dropwise over a five minute period. The reaction mixture was stirred twenty minutes more and was then partitioned between ethyl acetate-10% citric acid solution. The aqueous layer was extracted with ethyl acetate-and the combined organic extracts were washed with brine, dried (sodium sulfate), and roto-evaporated. Preparative thick layer chromatography of the crude reaction product on pre-coated silica gel plates (1 mm thickness, $CHCl_3$—$CH_3OH$ elution, 90:10 v/v) afforded the title compound as a solid: m.p. 139°–143° C. (d). HPLC=99% pure at 214 nm; TLC $R_f$=0.50 ($CH_2Cl_2$—$CH_3OH$—HOAc—$H_2O$, 90:10:1:1). NMR($CDCl_3$): Consistent with structure assignment and confirms presence of solvent. FAB MS: 592 (M+1). Analysis for $C_{32}H_{41}N_5O_6$•0.10 $CHCl_3$•0.50 EtOAc: Calculated: C, 63.24; H, 7.02; N, 10.81. Found: C, 63.25; H, 6.71; N, 10.58.

EXAMPLE 5

Synthesis of N-{(3R)-1,3-Dihydro-1-methyl-2-oxo-5-cyclohexyl-1H-1,4-benzodiazepin-3-yl}-N'-{[3-((2S)-amino-2-methoxycarbonyl)ethylphenyl]-urea}

A solution of 139 mg of N-{(3R)-1,3-dihydro-1-methyl-2-oxo-5-cyclohexyl-1H-1,4-benzodiazepin-3yl}-N'-{[3-((2S)-tert-butyloxycarbonylamino-2-methoxycarbonyl)ethylphenyl]-urea} in 10 mL of ethyl acetate was cooled to 0° C. under nitrogen. A steady stream of hydrogen chloride gas was passed through the reaction mixture for 10 minutes. The reaction vessel was sealed and the reaction mixture was stirred for an additional 30 minutes. All volatiles were removed under reduced pressure to give 143 mg of the title compound as a solid: m.p. 184° C. (d). HPLC=>98% pure at 214 nm; TLC $R_f$=0.50 ($CHCl_3$—$CH_3OH$—NHOH, 90:10:1). NMR(DMSO-$d_6$): Consistent with structure assignment and confirms presence of solvent. FAB MS: 492 (M+1). Analysis for $C_{26}H_{33}N_5O_4$•2.5 HCl•0.7 EtOAC: Calculated: C, 54.70; H, 6.55; N, 11.07. Found: C, 54.74; H, 6.19; N, 11.08.

EXAMPLE 6

Synthesis of
N-{(3R)-1,3-Dihydro-1-methyl-2-oxo-5-cyclohexyl-1H-1,4-benzodiazepin-3-yl }-N'-{[3-((2S )amino-2-carboxy)ethylphenyl]-urea}

Lithium hydroxide hydrate (26 mg) and 125 mg of N-{(3R)-1,3-dihydro-1-methyl-2-oxo-5-cyclohexyl-1H-1,4-benzodiazepin-3-yl}-N'-{[3-( (2S)-amino-2methoxycarbonyl)ethylphenyl]-urea} were combined in a tetrahydrofuran-water mixture (2:3, v/v) and stirred at room temperature for three hours. An additional 8 mg of lithium hydroxide hydrate was added and stirring was continued for 30 minutes more. The solvent was roto-evaporated and the crude product was purified by preparative reverse phase HPLC (Vydac C-18 column, acetonitrile-water (containing 0.1% trifluoroacetic acid), 8 mL/min flow rate, 45 minute gradient) to yield, after lyophilization, 59 mg of the title compound as a solid: m.p. 135°–139° C. (d). HPLC=99% pure at 214 nm. NMR(DMSO-$d_6$): Consistent with structure assignment and confirms presence of solvent. FAB MS: 478 (M+ +1). Analysis for $C_{25}H_{31}N_5O_4$•1.95 TFA•0.7 $H_2O$: Calculated: C, 50.40; H, 4.86; N, 9.83. Found: C, 50.37; H, 4.83; N, 10.10.

EXAMPLE 7

Synthesis of
N-{(3R)-1,3-Dihydro-1-methyl-2-oxo-5-phenyl-1H-1,4-benzodiazepin-3-yl}-N'-{[3-((1S)-tert-butyloxycarbonylamino-1-methoxycarbonyl)methylphenyl]-urea}

Part 1: (S)-Amino-(3-nitrophenyl)acetic acid (D)

A solution of L-phenylglycine (10 g) in 40 mL of conc. sulfuric acid was cooled in an ice water/acetone bath. 90% Nitric acid (3.72 mL) was added dropwise over a 30 minute period at such a rate as to keep the internal temperature below 10° C. After addition was complete, stirring was continued for 1 hour at 0° C. and then the reaction mixture was allowed to warm to room temperature over 1.5 hours. The reaction mixture was poured onto 200 g of crushed ice and the resulting mixture was neutralized with sodium hydroxide to pH 7. The reaction mixture was diluted with 600 mL of water, Celite was added and the resulting suspension was filtered and concentrated to give the crude product D contaminated with sodium sulfate. This material was taken to the next step without further purification.

Part 2: Methyl (S)-tert-Butyloxycarbonylamino-(3-nitrophenyl)acetate (E)

Crude (S)-amino-(3-nitrophenyl)acetic acid (66 mmole) was mixed with 2.64 g of sodium hydroxide in 150 mL of water. The resulting slurry was filtered and the filtrate was concentrated and redissolved in 50 mL of water. To this suspension was added 50 mL of tert-butanol, followed by the dropwise addition over a 30 minute period of 50 mL of tert-butanol containing 15.8 g of di-tert-butyldicarbonate. The reaction mixture was stirred at room temperature for 2 hours, was diluted with 250 mL of water, and then extracted with pentane (3×150 mL). The aqueous layer was acidified to pH 3 with sodium bisulfate approximately 9 g) and extracted with ethyl acetate. The combined organic extracts were dried ($Na_2SO_4$) and concentrated. The crude product was azeotropically dried with toluene to afford 12 g of the (S)-tert-butyloxycarbonylamino-(3-nitrophenyl)acetic acid. This material was dissolved in 110 mL of N,N-dimethylformamide and treated with 55 g (10 equivalents) of sodium bicarbonate and 20.5 mL of iodomethane. The resulting suspension was stirred under nitrogen for 1.5 hours, filtered, and concentrated under reduced pressure. The residual product was partitioned between ethyl acetate and water. The aqueous layer was extracted with ethyl acetate and the combined organic extracts were washed with brine, dried, and concentrated. Flash chromatography of the crude product on silica gel (ethyl acetate-hexane elution, 1:2 v/v) gave 11.07g of the pure title compound.

Part 3: Methyl (S)-tert-Butyloxycarbonylamino-(3-aminophenyl)acetate (F)

Methyl (S)-tert-butyloxycarbonylamino-(3-nitrophenyl)acetate (3 g) and 200 mg of 10% palladium on carbon catalyst were combined in 100 mL of methanol and hydrogenated on a Parr apparatus at 50 p.s.i. for 110 minutes. The reaction mixture was filtered and concentrated. The residue was azeotropically dried with toluene to give 2.4 g of the title compound.

Part 4: N-{(3R)-1,3-Dihydro-1-methyl-2-oxo-5-phenyl-1H-1,4-benzodiazepin-3-yl}-N'-{[3-((1S)tert-butyloxycarbonylamino-1-methoxycarbonyl)methylphenyl]urea}

By employing reaction conditions identical to those in Example 1, Part 3, a solution of methyl (S)-tert-butyloxycarbonylamino-(3-aminophenyl)acetate (F) (557 mg) in 50 mL of tetrahydrofuran was reacted with 197 mg of triphosgene, 832 mL of triethylamine, and 475 mg of 1,3-dihydro-1-methyl-3(R)-amino-5-phenyl-2H-1,4-benzodiazepin-2-one in 15 mL of tetrahydrofuran. The crude reaction product was flash chromatographed on silica gel (ethyl acetatehexane elution, 3:2 v/v) to give the title compound (989 mg) as a solid: m.p. 164°–166° C. (d). HPLC=99% pure at 214 nm; TLC $R_f$=0.51 (EtOAc-hexane,3:2). NMR(DMSO-$d_6$): Consistent with structure assignment and confirms presence of solvent. FAB MS: 572 (M++1). Analysis for $C_{31}H_{33}N_5O_6$•0.25 Hexane•0.6EtOAc: Calculated: C, 64.89; H, 6.44; N, 10.84. Found: C, 64.86; H, 6.59; N, 10.90.s

EXAMPLE 8

Synthesis of N-{(3R)-1,3-Dihydro-1-methyl-2-oxo-5-phenyl-1H-1,4-benzodiazepin-3-yl}-N'-{[3-((1S )-amino-1-methoxycarbonyl)methylphenyl]-urea}

Utilizing reaction conditions identical to those described in Example 2,737 mg of N-{(3R)-1,3-dihydro-1-methyl-2-oxo-5-phenyl-1H-1,4-benzodiazepin-3-yl}-N'-{[3-((1S)-tert-butyloxycarbonylamino-1-methoxycarbonyl)methylphenyl]-urea} was converted to the title compound which was obtained as a solid after chromatography on silica gel (chloroform: methanol:concentrated ammonium hydroxide, 90:10:1 v/v); yield 515 mg: m.p. 134°–136° C. (d). HPLC=99% pure at 214 nm; TLC $R_f$=0.40 (CHCl$_3$—CH$_3$OH—NH$_4$OH, 90:10:1). NMR(DMSO-$d_6$): Consistent with structure assignment and confirms presence of solvent. FAB MS: 472 (M++1). Analysis for $C_{26}H_{25}N_5O_4$•1.65 $H_2O$: Calculated: C, 62.30; H, 5.69; N, 13.97. Found: C, 62.24; H, 5.30; N, 14.32.

EXAMPLE 9

Synthesis of N-{(3R)-1,3-Dihydro-1-methyl-2-oxo-5-phenyl-1H-1,4-benzodiazepin-3-yl}-N'-{[3-((1S)-amino-1-carboxy)methylphenyl]-urea}

Lithium hydroxide hydrate (24 mg) and 255 mg of N-{(3R)-1,3-dihydro-1-methyl-2-oxo-5-phenyl-1H-1,4-benzodiazepin-3-yl}-N'-{[3-((1S)-amino-2-methoxycarbonyl)methylphenyl]-urea} were combined in a 1:1 tetrahydrofuran-water mixture (4 mL) and stirred at room temperature for thirty minutes. The solvent was roto-evaporated and the crude product was purified by preparative thick layer chromatography on pre-coated silica gel plates (0.5 mm thickness) (initial elution with CHCl$_3$—MeOH—HOAc—H$_2$O, 90:10:1:1, then double elution with CHCl$_3$—MeOH—HOAc—H$_2$O, 85:15:1.5:1.5). Two components were isolated from the silica gel plates. The higher $R_f$ component was further purified by preparative HPLC (Vydac C-18 column, acetonitrile-water (containing 0.1% trifluoroacetic acid), 8 mL/min flow rate,45 minute gradient) to give the title compound (39 mg) as a homogeneous white solid: m.p 191° C. (d). HPLC=99% pure at 214 nm, Rf=0.44 (EtOAc:pyridine:HOAc:H$_2$O; 10:5:1:3) NMR(DMSO-$d_6$): Consistent with structure assignment and confirms presence of solvent. FAB MS: 458 (M++1). Analysis for $C_{25}H_{23}N_5O_4$•1.55 TFA•0.65 $H_2O$: Calculated: C, 52.23; H, 4.03; N, 10.84. Found: C, 52.25; H, 4.06; N, 10.81.

EXAMPLE 10

Synthesis of N-{(3R)-1,3-Dihydro-1-methyl-2-oxo-5-phenyl-1H-1,4-benzodiazepin-3-yl}-N'-{[3-((1R)-amino-1-carboxy)methylphenyl]-urea}

Lithium hydroxide hydrate (24 mg) and 255 mg of N-{(3R)-1,3-dihydro-1-methyl-2-oxo-5-phenyl-1H-1,4-benzodiazepin-3-yl}-N'-{[3-((1S)-amino-2-methoxycarbonyl)methylphenyl]-urea} were combined in a 1:1 tetrahydrofuran-water mixture (4 mL) and stirred at room temperature for thirty minutes. The solvent was roto-evaporated and the crude product was purified by preparative thick layer chromatography on pre-coated silica gel plates (0.5 mm thickness) (initial elution with CHCl$_3$—MeOH—HOAc-H$_2$O, 90:10:1:1, then double elution with CHCl$_3$—MeOH—HOAc—H$_2$O, 85:15:1.5:1.5). Two components were isolated from the silica gel plates. The lower R$_f$ component was further purified by preparative HPLC (Vydac C-18 column, acetonitrile-water (containing 0.1% trifluoroacetic acid), 8 mL/min flow rate, 45 minute gradient) to give the title compound (8 mg) as a homogeneous white solid: m.p. 203°–204° C. (d). HPLC=99% pure at 214 nm, Rf=0.36(EtOAc:pyridine:HOAc:H$_2$O; 10:5:1:3) NMR(DMSO-d$_6$): Consistent with structure assignment and confirms presence of solvent. FAB MS: 458 (M+ +1). Analysis for C$_{25}$H$_{23}$N$_5$O$_4$•1.45 TFA•0.50 H$_2$O: Calculated: C, 53.02; H, 4.06; N, 11.08. Found: C, 53.05; H, 4.11; N, 10.96.

EXAMPLE 11

Synthesis of
N-{(3R)-1,3-Dihydro-1-methyl-2-oxo-5-phenyl-1H-1,4-benzodiazepin-3-yl}-N'-{[3-((1R,S)-tert-butyloxycarbonylamino-2-methoxycarbonyl)ethylphenyl]-urea}

Part 1: 3-Amino-3-(3-nitrophenyl)propionamide (G)

An autoclave was charged with 1.5 g of methyl 3-nitrophenylcinnamate, 15 mL of liquid ammonia, and 15 mL of 2-propanol. The autoclave was sealed and heated at 150° C. for 15 hours. The autoclave was cooled, vented, and the contents were concentrated under reduced pressure. The residual material was flash chromatographed on silica gel (chloroform-methanol-concentrated ammonium hydroxide elution, 90:10:1 v/v) to yield 617 mg of the title compound.

Part 2: Methyl 3-Amino-3-(3-nitrophenyl)propionate (H)

3-Amino-3-(3-nitrophenyl)propionamide (822 mg) and 12.3 g of Bio-Rad AG-MP-50 resin were combined in 25 mL of methanol and the resulting mixture was heated to reflux according to the literature procedure (J. Org. Chem. (1981) 46, 5351–5353). The crude reaction product was purified by flash chromatography (ethyl acetate elution) to yield 405 mg of the title compound.

Part 3: Methyl 3-tert-Butyloxycarbonylamino-3-(3-aminophenyl)propionate (I)

Methyl 3-amino-3-(3-nitrophenyl)propionate (400 mg) was dissolved in 5 mL of methylene chloride and treated with di-tert-butyldicarbonate (428 mg). The reaction mixture was protected from moisture and stirred at room temperature for one hour. Additional amounts of di-tert-butyldicarbonate (100 mg) were added to the reaction mixture after 1 and 2 hours, respectively. Finally, 131 μL of triethylamine was added and stirring was continued for 30 minutes more. The volatiles were removed under reduced pressure and the residual material was passed through a silica gel column (hexane-ethyl acetate elution, 1:1 v/v) to yield 423 mg of methyl 3-tert-butyloxycarbonylamino-3-(3-nitrophenyl)propionate. 383 mg of the latter compound was hydrogenated at atmospheric pressure employing 100 mg of 10% palladium on carbon catalyst in 15 mL of methanol. After two hours the reaction mixture was concentrated and the residue was azeotropically dried with toluene to give 333 mg of the title compound.

Part 4: Synthesis of N-{(3R)-1,3-Dihydro-1-methyl-2-oxo-5-phenyl-1H-1,4-benzodiazepin-3-yl}N'-{[3-((1R,S)-tert-butyloxycarbonylamino-2-methoxycarbonyl)ethylphenyl]-urea}

By employing reaction conditions identical to those in Example 1, Part 3, a solution of methyl 3-tert-butyloxycarbonylamino-3-(3-aminophenyl)propionate (I) (333 mg) in 28 mL of tetrahydrofuran was reacted with 112 mg of triphosgene, 472 μL of triethylamine, and 300 mg of 1,3-dihydro-1-methyl-3(R)-amino-5-phenyl-2H-1,4-benzodiazepin-2-one in 15 mL of tetrahydrofuran. The crude reaction product was flash chromatographed on silica gel (ethyl acetate elution) to give the title compound (551 mg) as a mixture of diasteriomers. The analytical material was obtained as a solid by dissolving the chromatographed material in ethyl acetate and precipitating it with hexane: m.p. 149°–151° C. HPLC=99% pure at 214 nm; TLC R$_f$=0.43 (CH$_2$Cl$_2$—CH$_3$OH—HOAc,90:10:1). NMR(DMSO-d$_6$): Consistent with structure assignment and confirms presence of solvent. FAB MS: 586 (M+ +1). Analysis for C$_{32}$H$_{35}$N$_5$O$_6$•0.2 Hexane•1.35 EtOAc: Calculated: C, 61.91; H, 6.95; N, 9.35. Found: C, 61.90; H, 6.71; N, 9.35.

EXAMPLE 12

Synthesis of
N-{(3R)-1,3-Dihydro-1-methyl-2-oxo-5-phenyl-1H-1,4-benzodiazepin-3-yl}-N,-{[3-((1R,S)-amino-2-methoxycarbonyl)ethylphenyl]-urea}

Utilizing reaction conditions identical to those described in Example 2,303 mg of N-{(3R)-1,3-dihydro-1-methyl-2-oxo-5-phenyl-1H-1,4-benzodiazepin-3-yl}-N'-{[3-((1R,S)-tert-butyloxycarbonylamino-2-methoxycarbonyl)ethylphenyl]-urea} was converted to the title compound which was obtained as a solid after chromatography on silica gel (chloroform-methanol elution, 9:1 v/v); yield 205 mg: m.p. 160°–162° C. (d): HPLC=98% pure at 214 nm; TLC R$_f$=0.25 (CH$_2$Cl$_2$—CH$_3$OH—HOAc—H$_2$O, 90:10:1:1). NMR(DMSO-d$_6$): Consistent with structure assignment and confirms presence of solvent. Analysis for C$_{26}$H$_{25}$N$_5$O$_4$•1.65 H$_2$O: Calculated: C, 63.89; H, 6.03; N, 12.94. Found: C, 63.90; H, 6.19; N, 12.96.

EXAMPLE 13

Synthesis of
N-{(3R)-1,3-Dihydro-1-methyl-2-oxo-5-phenyl-1H-1,4-benzodiazepin-3-yl}-N'-{[3-((1R,S)-amino-2-carboxy)ethylphenyl]-urea}

Lithium hydroxide hydrate (9 mg) and 100 mg of N-{(3R)-1,3-dihydro-1-methyl-2-oxo-5-phenyl-1H-1,4-benzodiazepin-3-yl}-N'-{[3-((1R,S)-amino-2methoxycarbonyl)ethylphenyl]-urea} were combined in 4 mL of a tetrahydrofuran-water mixture (1:1, v/v) and stirred at room temperature for two hours. An additional 5 mg of lithium hydroxide hydrate was added and stirring was continued for 60 minutes more. The solvent was roto-evaporated and the crude product was purified by preparative reverse phase HPLC (Vydac C-18 column, acetonitrile-water (containing 0.1% trifluoroacetic acid), 8 mL/min flow rate,45 minute gradient) to yield the title compound as a solid after lyophilization: m.p. 178° C. (d); (shrinks at 133° C.). HPLC=98% pure at 214 nm. NMR(DMSO-d$_6$): Consistent with structure assignment and confirms presence of solvent. FAB MS: 472 (M+ +1). Analysis for C$_{26}$H$_{25}$N$_5$O$_4$•2.0 TFA•0.3 H$_2$O: Calculated: C, 51.09; H, 3.94; N, 9.93. Found: C, 51.09; H, 3.63; N, 10.29.

EXAMPLE 14

Synthesis of
N-{(3R)-1,3-Dihydro-1-methyl-2-oxo-5-phenyl-1H-1,4-benzodiazepin-3-yl
}-N'-{[8-(methyl-2(R,S)-tert-butyloxycarbonylamino-1,2,3,4-tetrahydro-2-naphthoate)]-urea}

Part 1: R,S-5'-Nitrospiro[imidazolidine-4,2'(1H)-3',4'-dihydronaphthalene]-2, 5-dione; R,S-6'-nitrospiro[imidazolidine-4,2'(1H)-3',4'-dihydronaphthalene]-2, 5-dione; R,S-7'-nitrospiro[imidazolidine-4,2'(1H)-3',440 -dihydronaphthalene]-2,5-dione; and R,S-8'-nitrospiro[imidazolidine-4,2,(1H)-3',4'-dihydronaphthalene]-2,5-dione 7,8-Benzo-1,3-diazaspiro[4,5]decane-2,4-dione (20 g) was nitrated with 200 mL of 70% nitric acid according to the literature procedure in *J. Med. Chem.* (1987) 30, 542–547. Work-up of the reaction mixture afforded 20 g of a yellow solid which was characterized as a mixture of all four possible regioisomeric nitro derivatives.

Part 2: R,S-7'-Nitrospiro[imidazolidine-1-ethyl-4,2'-(3H)-3',4'-dihydronaphthalene]-2,5-dione and R,S-8'-Nitrospiro[imidazolidine-1-ethyl-4,2,-(3H)-3',4'-dihydronaphthalene]-2,5-dione (Mixture L); R,S-5'-Nitrospiro[imidazolidine-4,2'(1H)-3',4'-dihydronaphthalene]-2,5-dione and R,S-6'-nitrospiro[imidazolidine-4,2'(1H)-3',4'-dihydronaphthalene]-2,5-dione (Mixture M)

Four grams of the mixture obtained in Part 1, Example 14 was dissolved in 15.3 mL of 1N sodium hydroxide solution. The clear solution was concentrated to dryness under reduced pressure to give a solid which was azeotropically dried with toluene. This material was then combined with 900 mg of potassium iodide, 8.5 mL of ethyl bromide in 125 mL of absolute ethanol and heated to reflux for five hours. The solvent and excess reagent were removed in vacuo and the residue was partitioned between ethyl acetate and water. The organic phase was washed with water and brine, then dried (Na$_2$SO$_4$), and concentrated. The crude reaction product was then flash chromatographed on silica gel employing an ethyl acetate-hexane gradient (1:2 to 1:1 v/v) to yield 1.16 g of an chromatographically inseparable mixture of the title compounds, mixture L and 1.63 g of mixture M.

Part 3: Methyl 2-(R,S)-tert-Butyloxycarbonylamino-8-(amino-1,2,3,4-tetrahydro-2-naphthoate (O) and Methyl 2-(R,S)-tert-Butyloxycarbonylamino-7-(amino-1,2,3,4-tetrahydro-2-naphthoate (P)

Mixture L (400 mg) was combined with 10 mL of 12N hydrochloric acid and heated to 140° C. in a sealed tube for three days. Concentration of the reaction mixture afforded 335 mg of the corresponding amino acid hydrolyzation products. This material was dissolved in 2.22 mL of 1N sodium hydroxide solution and treated in succession with 266 mg of di-tert-butyl dicarbonate, 5 mL of water, and 5 mL of tert-butanol. The pH of the reaction mixture was adjusted to 8–8.5 with the addition of sodium hydroxide solution. After 1 hour, an additional 100 mg of di-tert-butyl dicarbonate was added and stirring was continued for 20 minutes more. The reaction mixture was washed with pentane, rendered acidic to pH 3 with potassium hydrogen sulfate, and extracted with ethyl acetate. The combined organic extracts were washed with brine, then dried (Na$_2$SO$_4$), and concentrated to give the protected amino acids. This material (104 mg) was dissolved in 5 mL of N,N-dimethylformamide and treated with 10 equivalents of solid sodium bicarbonate and 97 μL (5 equivalents) of iodomethane. After stirring 90 minutes at room temperature, an additional 97 μL of iodomethane was added. The reaction mixture was filtered after one hour, concentrated and the residue was partitioned between ethyl acetate and water. The crude product was chromatographed on pre-coated silica gel plates (1 mm thickness, hexane-ethyl acetate elution, 1:1 v/v) to yield the protected methyl esters as a chromatographically inseparable mixture. This material (60 mg) was hydrogenated at atmospheric pressure in 5 mL of methanol in the presence of 30 mg of 10% on carbon palladium catalyst. After 60 minutes the reaction mixture was filtered and the mixture was purified by preparative thick layer chromatography on pro-coated silica gel plates (0.5 mm thickness, hexane-ethyl acetate elution, 1:1 v/v) to afford 15 mg of the title compound 0 and 33 mg of the title compound P.

Part4: Methyl 2-(R,S)-tert-Butyloxycarbonylamino-6-(amino-1,2,3,4-tetrahydro-2-naphthoate (Q) and Methyl 2-(R,S)-tert-Butyloxycarbonylamino-5-(amino-1,2,3,4-tetrahydro-2-naphthoate (R)

By employing reaction conditions identical to those described in Part 3, Example 14, mixture M (500 mg) was transformed in the prescribed manner to give 30 mg of title compound Q and 44 mg of title compound R.

Part 5: N-{(3R)-1,3-Dihydro-1-methyl-2-oxo-5-phenyl-1H-1,4-benzodiazepin-3-yl}-N,-{[8-(methyl-2-(R,S)-tert-butyloxycarbonylamino-1,2,3,4-tetrahydro-2-naphthoate)]-urea}

By employing reaction conditions identical to those in Example 1, Part 3, a solution of methyl 2-(R,S)-tert-butyloxycarbonylamino-8-(amino-1,2,3,4-tetrahydro-2-naphthoate (0) (15 mg) in 1 mL of tetrahydrofuran was reacted with 4.6 mg of triphosgene, 20 μL of triethylamine, and 14 mg of 1,3-dihydro-1-methyl-3(R)-amino-5-phenyl-2H-1,4-benzodiazepin-2-one. The crude reaction product was purified by preparative thick layer chromatography on pre-coated silica gel plates (0.5 mm thickness, chloroform-methanol elution, 9:1 v/v) to give the title compound as a mixture of diasteriomers: m.p. 185°–189° C. HPLC=97.7% pure at 214 run. NMR(DMSO-d$_6$): Consistent with structure assignment and confirms presence of solvent. FAB MS: 612 (M+ +1). Analysis for C$_{34}$H$_{36}$N$_5$O$_6$•0.5 H$_2$O: Calculated: C, 65.90; H, 6.02; N, 11.30. Found: C, 65.93; H, 6.22; N, 11.14.

EXAMPLE 15

Synthesis of
N-{(3R)-1,3-Dihydro-1-methyl-2-oxo-5-phenyl-1H-1,4-benzodiazepin-3-yl}-N'-{[7-(methyl-2-(R,S)-tert-butyloxycarbonylamino-1,2,3,4-tetrahydro-2-naphthoate)]-urea}

By employing reaction conditions identical to those in Example 1, Part 3, a solution of methyl 2-(R,S)-tert-butyloxycarbonylamino-7-(amino-1,2,3,4-tetrahydro-2-naphthoate (P) (33 mg) in 2.5 mL of tetrahydrofuran was reacted with 10 mg of triphosgene, 43 μL of triethylamine, add 30 mg of 1,3-dihydro-1-methyl-3(R)-amino-5-phenyl-2H-1,4-benzodiazepin-2one. The crude reaction product was purified by preparative thick layer chromatography on pre-coated silica gel plates (0.5 mm thickness, chloroform-methanol elution, 9:1 v/v) to give 40 mg of the title compound as a mixture of diasteriomers: m.p. 181°–185° C. HPLC=>99% pure at 214 nm. NMR(DMSO-d$_6$): Consistent with structure assignment and confirms presence of solvent. FAB MS:

612 (M++1). Analysis for $C_{34}H_{36}N_5O_6$•0.2 $CHCl_3$: Calculated: C, 64.73; H, 5.75; N, 11.04. Found: C, 64.97; H, 6.07; N, 10.69.

EXAMPLE 16

Synthesis of
N-{(3R)-1,3-Dihydro-1-methyl-2-oxo-5-phenyl-1H-1,4-benzodiazepin-3-yl}-N'-{[7-(methyl-2-(R,S)-amino-1,2,3,4-tetrahydro-2-naphthoate)]-urea}

Utilizing reaction conditions identical to those described in Example 2, 38 mg of N-{(3R)-1,3-dihydro-1-methyl-2-oxo-5-phenyl-1H-1,4-benzodiazepin-3-yl}-N'-{[7-(methyl-2-(R,S)-tert-butyloxy-carbonylamino-1,2,3,4-tetrahydro-2-naphthoate)]-urea} was converted to the title compound which was obtained as a solid: m.p. 213°-218° C. (d). HPLC=99% pure at 214 nm; TLC $R_f$=0.52 ($CHCl_3$—$CH_3OH$—$NH_4OH$, 90:10:1). NMR(DMSO-$d_6$): Consistent with structure assignment and confirms presence of solvent. FAB MS: 512 (M+1). Analysis for $C_{29}H_{29}N_5O_4$•2.6 $H_2O$•1.0 HCl•0.6 $CHCl_3$: Calculated: C, 56.43; H, 5.57; N, 11.12. Found: C, 56.45; H, 5.60; N, 10.76.

EXAMPLE 17

Synthesis of
N-{(3R)-1,3-Dihydro-1-methyl-2-oxo-5-phenyl-1H-1,4-benzodiazepin-3-yl}-N'-{[7-(2-(R,S)amino-1,2,3,4-tetrahydro-2-naphthoic acid)]-urea}

Utilizing reaction conditions identical to those described in Example 6, 37 mg of N-{(3R)-1,3-dihydro-1-methyl-2-oxo-5-phenyl-1H-1,4-benzodiazepin-3-yl}-N'-{[7-(methyl-2-(R,S)-amino-1,2,3,4-tetrahydro-2-naphthoate)]-urea} was converted to the title compound which was obtained as a solid after preparative HPLC chromatography: m.p. 199° C. (d). HPLC=>94% pure at 214 nm; TLC $R_f$=0.67 (EtOAc-pyridine-HOAc—$H_2O$, 10:5:1:3 v/v). NMR(DMSO-$d_6$): Consistent with structure assignment and confirms presence of solvent. FAB MS: 498 (M+1). Analysis for $C_{28}H_{27}N_5O_4$•1.25 $H_2O$ •1.0 TFA: Calculated: C, 56.83; H, 4.85; N, 11.04. Found: C, 56.80; H, 4.84; N, 10.67.

EXAMPLE 18

Synthesis of
N-{(3R)-1,3-Dihydro-1-methyl-2-oxo-5-phenyl-1H-1,4-benzodiazepin-3-yl}-N'-{[6-(methyl-2-(R,S)-tert-butyloxycarbonylamino-1,2,3,4-tetrahydro-2-naphthoate)]-urea}

By employing reaction conditions identical to those in Example 1, Part 3, a solution of methyl 2-(R,S)-tert-butyloxycarbonylamino-6-(amino-1,2,3,4-tetrahydro-2-naphthoate (Q) (30 mg) in 2.0 mL of tetrahydrofuran was reacted with 10 mg of triphosgene, 39 µL of triethylamine, and 27 mg of 1,3-dihydro-1-methyl-3(R)-amino-5-phenyl-2H-1,4-benzodiazepin-2one. The crude reaction product was purified by preparative thick layer chromatography on pre-coated silica gel plates (1.0 nun thickness, chloroform-methanol elution, 9:1 v/v) to give 36 mg of the title compound as a mixture of diasteriomers:.m.p. 173°-178° C. HPLC=99% pure at 214 nm. NMR(DMSO-$d_6$): Consistent with structure assignment and confirms presence of solvent. FAB MS: 612 (M++1). Analysis for $C_{34}H_{36}N_5O_6$•0.7 $H_2O$: Calculated: C, 65.41; H, 6.20; N, 11.22. Found: C, 65.44; H, 6.08; N, 10.90.

EXAMPLE 19

Synthesis of
N-{(3R)-1,3-Dihydro-1-methyl-2-oxo-5-phenyl-1H-1,4-benzodiazepin-3-yl}-N'-{[6-(methyl-2-R,S)-amino-1,2,3,4-tetrahydro-2-naphthoate)]-urea}

Utilizing reaction conditions identical to those described in Example 2, 30 mg of N-{(3R)-1,3-dihydro-1-methyl-2-oxo-5-phenyl -1H-1,4-benzodiazepin-3-yl}-N,-{[6-(methyl-2-(R,S)-tert-butyloxycarbonyl- amino-1,2,3,4-tetrahydro-2-naphthoate)]-urea} was converted to the title compound which was obtained as a solid. HPLC=>99% pure at 214 nm. NMR(DMSO-$d_6$): Consistent with structure assignment and confirms presence of solvent. FAB MS: 512 (M+1).

EXAMPLE 20

Synthesis of
N-{(3R)-1,3-Dihydro-1-methyl-2-oxo-5-phenyl-1H-1,4-benzodiazepin-3-yl }-N'-{[6-(2-(R,S)-amino-1,2,3,4-tetrahydro-2-naphthoic acid)]-urea}

Utilizing reaction conditions identical to those described in Example 6, 27 mg of N-{(3R)-1,3-dihydro-1-methyl-2-oxo-5-phenyl-1H-1,4-benzodiazepin-3-yl}-N'-{[6-(methyl-2-(R,S)-amino-1,2,3,4-tetrahydro-2-naphthoate) ]-urea} was converted to the title compound which was obtained as a solid after preparative HPLC chromatography: m.p. 196° C. (d). HPLC=>99% pure at 214 nm. NMR(DMSO-$d_6$): Consistent with structure assignment and confirms presence of solvent. FAB MS: 498 (M+1). Analysis for $C_{28}H_{27}N_5O_4$•1.55 $H_2O$ •0.85 TFA: Calculated: C, 54.17; H, 4.42; N, 10.16. Found: C, 54.17; H, 4.40; N, 10.27.

EXAMPLE 21

Synthesis of
N-{(3R)-1,3-Dihydro-1-methyl-2-oxo-5-phenyl-1H-1,4-benzodiazepin-3-yl}-N'-{[5-(methyl-2-(R,S)-tert-butyloxycarbonylamino-1,2,3,4-tetrahydro-2-naphthoate)]-urea}

By employing reaction conditions identical to those in Example 1, Part 3, a solution of methyl 2-(R,S)-tert-butyloxycarbonylamino-5-(amino-1,2,3,4-tetrahydro-2-naphthoate (R) (4 mg) in 3.0 mL of tetrahydrofuran was reacted with 14 mg of triphosgene, 57 µL of triethylamine, and 40 mg of 1,3-dihydro-1-methyl-3(R)-amino-5-phenyl-2H-1,4-benzodiazepin-2one. The crude reaction product was purified by preparative thick layer chromatography on pre-coated silica gel plates (1.0 mm thickness, chloroform-methanol elution, 9:1 v/v) to give 54 mg of the title compound as a mixture of diasteriomers: m.p. 171°-175° C. HPLC=99% pure at 214 rim. NMR(DMSO-$d_6$): Consistent with structure assignment and confirms presence of solvent. FAB MS: 612 (M++1). Analysis for $C_{34}H_{36}N_5O_6$•0.25 $H_2O$ •0.8$CHCl_3$: Calculated: C, 58.73; H, 5.42; N, 9.84. Found: C, 58.73; H, 5.45; N, 9.87.

EXAMPLE 22

Synthesis of
N-{(3R)-1,3-Dihydro-1-methyl-2-oxo-5-phenyl-1H-1,4-benzodiazepin-3-yl}-N'-{[5-(methyl-2-(R,S)-amino-1,2,3,4-tetrahydro-2-naphthoate)]-urea}

Utilizing reaction conditions identical to those described in Example 2, 49 mg of N-{(3R)-1,3-dihydro-1- methyl-2-oxo-5-phenyl-1H-1,4-benzodiazepin-3-yl}-N,-{[5-(methyl-2-(R,S)-tert-butyloxycarbonylamino-1,2,3,4-tetrahydro-2-naphthoate)]-urea} was converted to the title compound which was obtained as a solid. HPLC=99% pure at 210 nm. NMR(DMSO-d$_6$): Consistent with structure assignment and confirms presence of solvent. FAB MS: 512 (M+1). Analysis for C$_{29}$H$_{29}$N$_5$O$_4$•2.7 H$_2$O •2.0 HCl •0.6 EtOAc: Calculated: C, 54.98; H, 6.05; N, 10.21. Found: C, 54.99; H, 5.66; N, 10.13.

EXAMPLE 23

Synthesis of N-{(3R)-1,3-Dihydro-1-methyl-2-oxo-5-phenyl-1H-1,4-benzodiazepin-3-yl}-N'-{[5-(2-(R,S)-amino-1,2,3,4-tetrahydro-2-naphthoic acid)]-urea}

Utilizing reaction conditions identical to those described in Example 6, 46 mg of N-{(3R)-1,3-dihydro-1-methyl-2-oxo-5-phenyl-1H-1,4-benzodiazepin-3-yl}-N'-{[5-(methyl-2-(R,S)-amino-1,2,3,4-tetrahydro-2-naphthoate)]-urea} was converted to the title compound which was obtained as a solid after preparative HPLC chromatography: m.p. 189° C. (d). HPLC=>99% pure at 210 nm. NMR(DMSO-d$_6$): Consistent with structure assignment and confirms presence of solvent. FAB MS: 498 (M+1). Analysis for C$_{28}$H$_{27}$N$_5$O$_4$•0.95 H$_2$O •1.9 TFA: Calculated: C, 52.23; H, 4.25; N, 9.58. Found: C, 52.24; H, 4.24; N, 9.87.

What is claimed is:

1. A compound of Formula I:

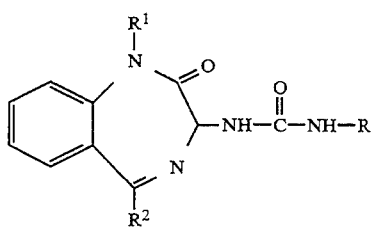

wherein:
R is

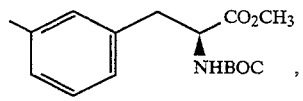

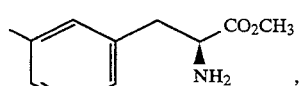

-continued

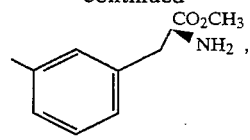

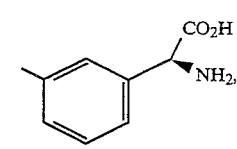

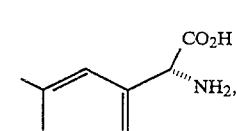

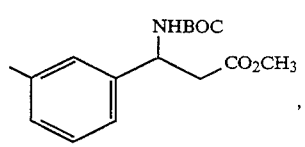

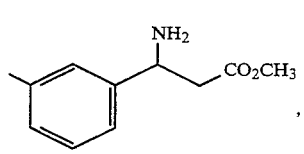

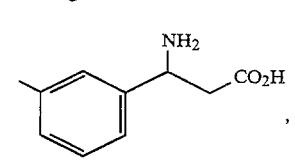

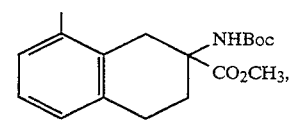

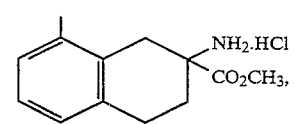

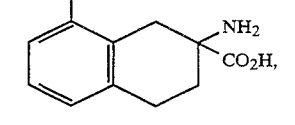

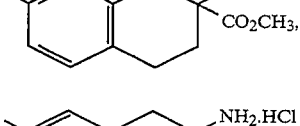

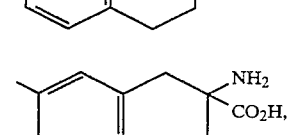

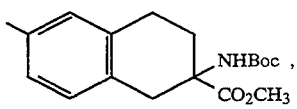
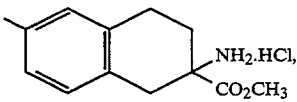
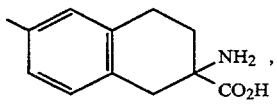
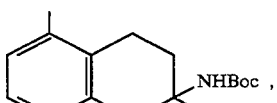
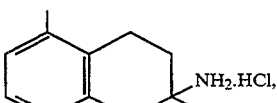
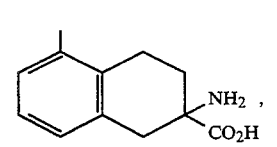
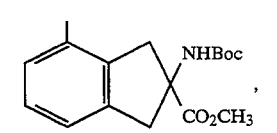
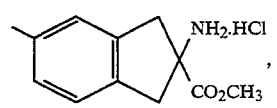
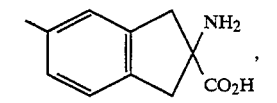
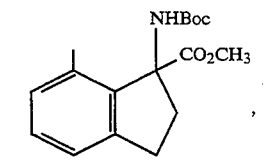
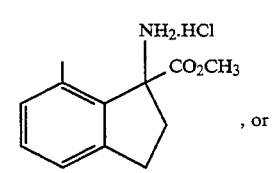, or

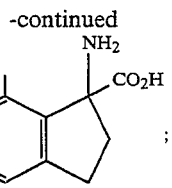;

$R^1$ is $C_1$–$C_6$ linear or branched chain alkyl or cyclopropyl;

$R^2$ is unsubstituted or substituted phenyl where the substituent is fluoro, chloro, bromo, iodo, nitro, carboxy, hydroxy, amino, hydroxy $C_1$–$C_4$-alkyl, $C_1$–$C_4$-mono or di-alkyl amino; or cyclohexyl;

or the optical isomers, prodrugs or pharmaceutically acceptable salts thereof.

2. The compound of claim 1 which is:

N-{(3R )-1,3-Dihydro-1-methyl-2-oxo-5-phenyl-1H-1,4-benzodiazepin-3-yl}-N'-{[3-((2S)-tertbutyloxycarbonylamino-2-methoxycarbonyl)ethylphenyl]urea}, N-{(3R)-1,3-Dihydro-1-methyl-2-oxo-5-phenyl-1H-1,4-benzodiazepin-3-yl}-N'-{[3-((2S)-amino-2-methoxycarbonyl)ethylphenyl]-urea}, N-{(3R)-1,3-Dihydro-1-methyl-2-oxo-5-phenyl-1H-1,4-benzodiazepin-3-yl}-N'-{[3-((2S)-amino-2-carboxy)ethylphenyl]-urea}, N-{(3R)-1,3-Dihydro-1-methyl-2-oxo-5-cyclohexyl-1H-1,4-benzodiazepin-3-yl}-N'-{[3-((2S)-tert-butyloxycarbonylamino-2-methoxycarbonyl)ethylphenyl]-urea}, N-{(3R)-1,3-Dihydro-1-methyl-2-oxo-5-cyclohexyl-1H-1,4-benzodiazepin-3-yl}-N'-{[3-((2S)-amino-2methoxycarbonyl)ethylphenyl]-urea}, N-{(3R)-1,3-Dihydro-1-methyl-2-oxo-5-cyclohexyl-1H-1,4-benzodiazepin-3-yl}-N'-{[3-((2S)-amino-2-carboxy)ethylphenyl]-urea}, N-{(3R)-1,3-Dihydro-1-methyl-2-oxo-5-phenyl-1H-1,4-benzodiazepin-3-yl}-N'-{[3-( (1S)-tert-butyloxycarbonylamino-1-methoxycarbonyl)methylphenyl]-urea}, N-{(3R)-1,3-Dihydro-1-methyl-2-oxo-5-phenyl-1H-1,4-benzodiazepin-3-yl}-N'-{[3-((1S)-amino-1methoxycarbonyl)methylphenyl]-urea}, N-{(3R)-1,3-Dihydro-1-methyl-2-oxo-5-phenyl-1H-1,4-benzodiazepin-3-yl}-N'-{[3-((1S)-amino-1-carboxy)methylphenyl]-urea}, N-{(3R)-1,3-Dihydro-1-methyl-2-oxo-5-phenyl-1H-1,4-benzodiazepin-3-yl}-N'-{[3-((1R)-amino-1-carboxy)methylphenyl]-urea}, N-{(3R)-1,3-Dihydro-1-methyl-2-oxo-5-phenyl-1-H1,4-benzodiazepin-3-yl}-N'-{[3-((1R,S)-tert-butyloxycarbonylamino-2-methoxycarbonyl)ethylphenyl]-urea}, N-{(3R)- 1,3-Dihydro-1-methyl-2-oxo- 5-phenyl-1H-1,4-benzodiazepin-3-yl }-N'-{[3-((1R, S)-amino-2methoxycarbonyl)ethylphenyl]-urea}, N-{(3R)-1,3-Dihydro-1-methyl-2-oxo-5-phenyl-1H-1,4-benzodiazepin-3-yl}-N'-{[3-( (1R,S)-amino-2carboxy)ethylphenyl]-urea}, N-{(3R)-1,3-Dihydro-1-methyl-2-oxo-5-phenyl-1H-1,4-benzodiazepin-3-yl}-N'-{[8-(methyl-2-(R,S)-tert-butyloxycarbonylamino-1,2,3,4-tetrahydro-2-naphthoate)]-urea}, N-{(3R)-1,3-Dihydro-1-methyl-2-oxo-5-phenyl-1H-1,4-benzodiazepin-3-yl}-N'-{[7-(methyl-2-(R,S)- tert-butyloxycarbonylamino-1,2,3,4-tetrahydro-2-naphthoate)]-urea},

N-{(3R)-1,3-Dihydro-1-methyl-2-oxo-5-phenyl-1H-1,4-benzodiazepin-3-yl}-N'-{[7-(methyl-2-(R, S)-amino-1,2,3,4-tetrahydro-2-naphthoate)]-urea}, N-{(3R)-1,3-Dihydro-1-methyl-2-oxo-5-phenyl-1H-1,4-benzodiazepin-3-yl}-N'-{[7-(2-(R,S)-amino-1,2,3,4-tetrahydro-2-naphthoic acid)]-urea}, N-{(3R)-1,3-Dihydro-1-methyl-2-oxo-5-phenyl-1H-1,4-benzodiazepin-3-yl }-N'-{[6-(methyl-2-(R, S)-tert-butyloxycarbonylamino-1,2,3,4-tetrahydro-2-naphthoate)]-urea}, N-{(3R)-1,3-Dihydro-1-methyl-2-oxo-5-phenyl-1H-1,4-benzodiazepin-3-yl}-N'-{[6-(methyl-2-(R,S)-amino-1,2,3,4-tetrahydro-2-naphthoate)]-urea}, N-{(3R)-1,3-Dihydro-1-methyl-2-oxo-5-phenyl-1H-1,4-benzodiazepin-3-yl }-N'-{[6-(2-(R, S)-amino-1,2,3,4-tetrahydro-2-naphthoic acid)]-urea}, N-{(3R)-1,3-Dihydro-1-methyl-2-oxo-5-phenyl-1H-1,4-benzodiazepin-3-yl}-N'-{[5-(methyl-2-(R, S)-tert-butyloxycarbonylamino-1,2,3,4-tetrahydro-2-naphthoate)]-urea}, N-{(3R)-1,3-Dihydro-1-methyl-2-oxo-5-phenyl-1H-1,4-benzodiazepin-3-yl }-N'-{[5-(methyl-2-(R, S)-amino-1,2,3,4-tetrahydro-2-naphthoate)]-urea}, N-{(3R)-1,3-Dihydro-1-methyl-2-oxo-5-phenyl-1H-1,4-benzodiazepin-3-yl}-N'-{[5-(2-(R, S)-amino-1,2,3,4-tetrahydro-2-naphthoic acid)]-urea}, or the pharmaceutically acceptable salts thereof.

3. The compound of claim 1 which is:

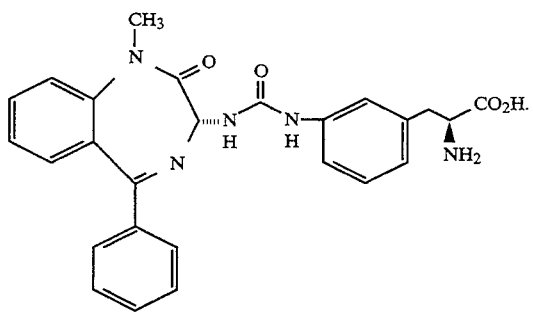

4. The compound of claim 1 which is:

5. The compound of claim 1 which is:

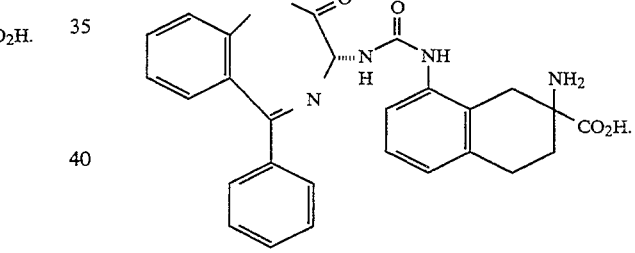

6. The compound of claim 1 which is:

7. The compound of claim 1 which is:

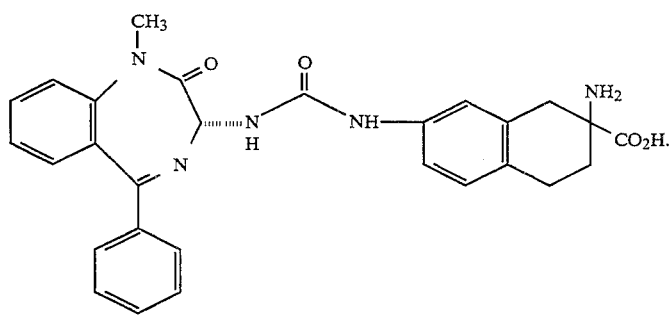

8. The compound of claim 1 which is:

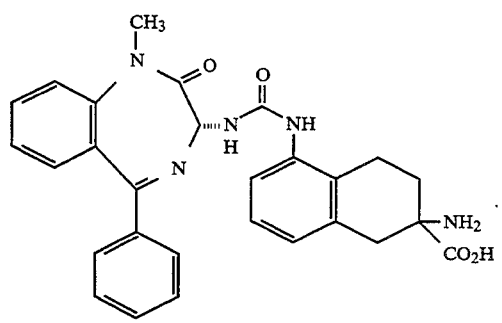
9. The compound of claim 1 which is:
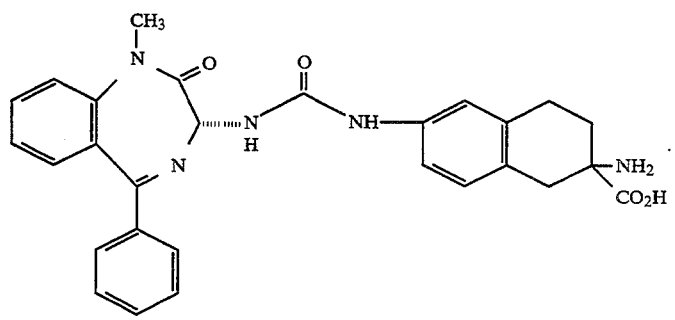
10. The compound of claim 1 which is:
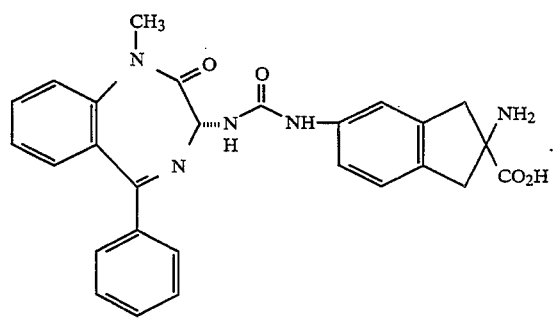
11. The compound of claim 1 which is:
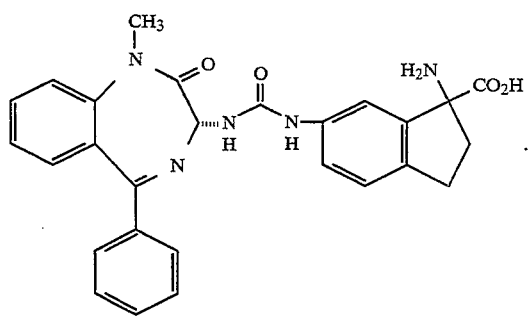
12. The compound of claim 1 which is:
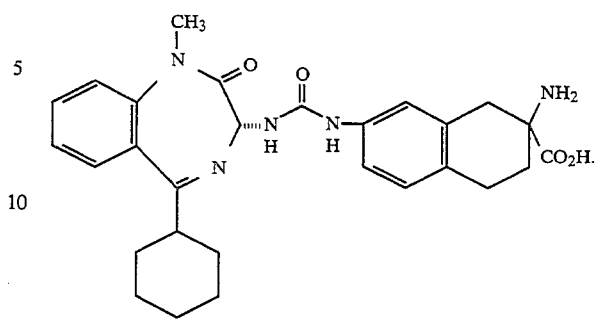
13. The compound of claim 1 which is:
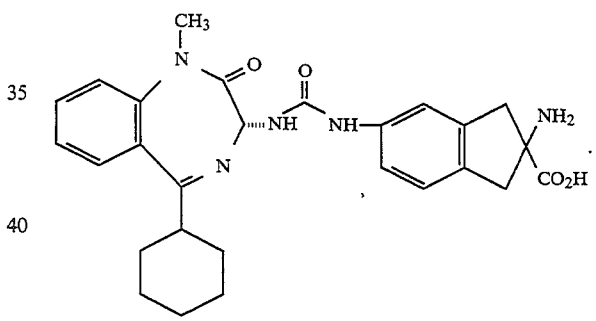
14. The compound of claim 1 which is:
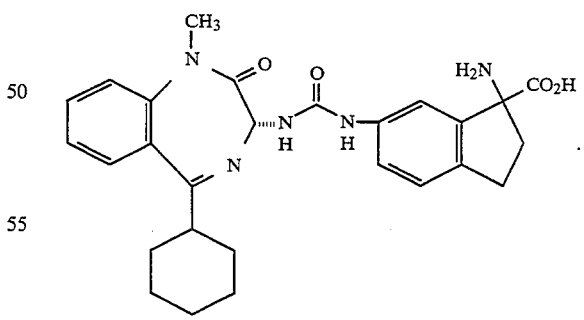
* * * * *